US007320981B2

(12) United States Patent
Morris et al.

(10) Patent No.: US 7,320,981 B2
(45) Date of Patent: Jan. 22, 2008

(54) VARIOLIN DERIVATIVES AS ANTI-CANCER AGENTS

(75) Inventors: Jonathan Charles Morris, Christchurch (NZ); Regan James Anderson, Christchurch (NZ); Modesto Remuiñán, Madrid (ES); Ignacio Manzanares, Madrid (ES)

(73) Assignee: Pharma Mar, S.A., Madrid (ES)

( * ) Notice: Subject to any disclaimer, the term of this patent is extended or adjusted under 35 U.S.C. 154(b) by 366 days.

(21) Appl. No.: 10/332,562

(22) PCT Filed: Jul. 11, 2001

(86) PCT No.: PCT/GB01/03111

§ 371 (c)(1),
(2), (4) Date: Jun. 25, 2003

(87) PCT Pub. No.: WO02/04447

PCT Pub. Date: Jan. 17, 2002

(65) Prior Publication Data

US 2005/0014778 A1 Jan. 20, 2005

(30) Foreign Application Priority Data

Jul. 11, 2000 (GB) .............................. 0017055.5
Dec. 15, 2000 (GB) .............................. 0030689.4

(51) Int. Cl.
*C07D 471/14* (2006.01)
*A61K 31/505* (2006.01)

(52) U.S. Cl. ...................................... 514/267; 544/250
(58) Field of Classification Search ................ 544/250; 514/267
See application file for complete search history.

(56) References Cited

U.S. PATENT DOCUMENTS

2004/0058939 A1* 3/2004 Alvarez et al. ............. 514/267

FOREIGN PATENT DOCUMENTS

WO   WO 02/12240   2/2002
WO   WO 03/006457  1/2003

OTHER PUBLICATIONS

Alvarez, M. et al., "Synthesis of deoxyvariolin B", *Tetrahedron Letters*, 42(2), pp. 315-317 (2001).
Alvarez, Mercedes et al., "Synthesis of 1, 2-dihydropyrrolo[1,2-c]pyrimidin-1-ones", *J. Chem. Soc. Perkins Trans. I*, pp. 249-255 (1999).
Alvarez, Mercedes et al., "Synthesis of 3-Aryl- and 3-Heteroaryl-7-azaindoles", *Synthesis*, pp. 615-620 (1999).
Anderson,R.J. et al., "Studies toward the total synthesis of the variolins: rapid entry to the core structure", *Tetrahedron Lett.*, vol. 42(2), pp. 311-313 (2001).

Capuano, Lilly et al., "(Heterocyclizations, XIII) New Polycyclic Pyrimidines with Bridge-Head Nitrogen", *Chem. Ber.*, 107, pp. 929-936 (1974).
Desarbre, Eric et al., "Synthesis of 2-Substituted-1H-Pyrrolo[2,3-b] Pyridines: Preparation of 7-Azaolivacine Analogue and 7-Azaindolopyridopyrimidine Derivatives", *Tetrahedron*, 53(10), pp. 3637-3648 (1997).
Erba et al., "Cell cycle phase perturbation and apoptosis induced by Variolin B, a novel antitumor agent of marine origin", *Proc. Am. Assoc. Can. Res. Annual Meeting*, vol. 27, #198 pp. 28-29 (1996).
Fresneda, Pilar M. et al., "Synthetic studies towards the 2-aminopyrimidine alkaloids variolins and meridianins from marine origin", *Tetrahedon Lett.*, 41(24), pp. 4777-4780 (2000).
Girgis, Nabih S. et al., "The Synthesis of 5-Azaindoles by Substitution-Rearrangement of 7-Azaindoles upon Treatment with Certain Primary Amines", *J. Heterocyclic Chem.*, vol. 26, No. 2, pp. 317-325 (1989).
Katritzky, Alan R. et al, *Comprehensive Heterocyclic Chemistry*, Pergamon Press, Oxford, vol. 3, p. 111 (1984).
Katritzky, Alan R. et al., "Activation of the 2-Alkyl Group of a 2-Alkylindole toward Proton Loss and Subsequent Electrophilic Substitution", *J. Am. Chem. Soc.*, vol. 108, No. 21, pp. 6808-6809 (1986).
Lorenz et al. "A New Indole Synthesis[1]", *J. Org. Chem.*, vol. 30, pp. 2531-2533 (1965).
Majeed, Amera J. et al., "Stannylation Reactions and Cross-Couplings in Pyrimidines", *Tetrahedron*, vol. 45, No. 4, pp. 993-1006 (1989).

(Continued)

*Primary Examiner*—Deepak Rao
(74) *Attorney, Agent, or Firm*—Fish & Richardson P.C.

(57) ABSTRACT

The invention provides variolin derivatives of formula (I), wherein: $R_1$ and $R_2$ are each independently selected from the group consisting of H, OH, OR, SH, SR, SOR, $SO_2R$, $NO_2$, $NH_2$, NHR, $N(R)_2$, NHCOR, $N(COR)_2$, $NHSO_2R$, CN, halogen, C(=O)H, C(=O)R, $CO_2H$, $CO_2R$, $C_1$-$C_{12}$ alkyl, $C_1$-$C_{12}$ haloalkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic; and $R_3$ is selected from the group consisting of H, OH and OMe; wherein the or each group R is independently selected from the group consisting of OH, $C_1$-$C_{12}$ alkyl, $C_1$-$C_{12}$ haloalkyl, $C_2$-$C_{12}$ alkenyl, $C_2$-$C_{12}$ alkynyl, substituted or unsubstituted aryl, substituted unsubstituted aralkyl, substituted or unsubstituted arylalkenyl and substituted or unsubstituted heteroaromatic, and wherein the group $R_1$, $R_2$ or $R_3$ is a group of formula $N(R)_2$ or $N(COR)_2$, each of the R groups may be the same or different, or the two R groups, together with the nitrogen atom to which they are attached, may form a 5-14 membered heterocyclic ring. These compounds display activity against a range of mammalian cancer cell lines. New synthetic routes to new and known variolin compounds, together with novel intermediates, are also disclosed. New antitumour activity of known variolin compounds is also described.

45 Claims, No Drawings

OTHER PUBLICATIONS

Mendiola, Javier et al., "Reaction of 2-Bromomethylazoles and TosMIC: A Domino Process to Azolopyrimidines. Synthesis of Core Tricycle of the Variolins Alkaloids", *Organic Letters,* vol. 2, No. 21, pp. 3253-3256 (2000).

Perry, Nigel B. et al., "Alkaloids from the Antarctic sponge *Kirkpatrickia varialosa.* Part 1: Variolin B, a new antitumor and antiviral compound" *Tetrahedron,* 50(13), pp. 3987-3992 (1994).

Sawayama, Tadahiro et al., "Displacement Reactions of 2-Alkylsulfonyl-4-Chloropyrimidine Derivatives with Nucleophiles", *Heterocycles,* vol. 8, pp. 299-305 (1977).

Perry, Nigel B. et al., "Alkaloids from the Antarctic Sponge *Kirkpatrickia varialosa.* Part 2: Variolin A and N(3')-methyl tetrahydrovariolin B", *Tetrahedron,* vol. 50, No. 13, pp. 3993-4000 (1994).

Vorbrüggen et al., "Sysntheses of Nucleosides—Amination of Heterocycles—A New Simple Synthesis of Cytidines", *Liebigs Annalen Der Chemie,* pp. 988-1002 (1975).

Calabresi et al., "Chemotherapy of Neoplastic Diseases", Goodman & Gilman's The Pharmacological Basis of Therapeutics, 9th ed. New York: McGraw-Hill, 1996, pp. 1225-1229.

Charya et al., "Wynthesis and Evaluation of Sulphonylhydrazones of Phthalimido Acetaldehyde as Anticancer Agents", J. Indian Chem Soc., vol. 75, pp. 46-48 (1998).

* cited by examiner

VARIOLIN DERIVATIVES AS ANTI-CANCER AGENTS

This application is a 371 of PCT/GB01/03111 file Jul. 11, 2001.

FIELD OF THE INVENTION

The present invention relates to antitumoural compounds, and in particular to new antitumoural analogs of variolin B and deoxyvariolin B. The present invention also relates to synthetic processes, and in particular to synthetic processes for producing both the new compounds of the invention and the known compounds variolin B and deoxyvariolin B, including novel intermediates which form a part of such synthetic processes. In addition, the present invention relates to novel, previously undisclosed indications of known variolin compounds.

BACKGROUND OF THE INVENTION

The variolins are a new class of marine alkaloids isolated from the rare, difficult to access Antarctic sponge *Kirkpatricka varialosa*, with Variolin B (1) being a typical example.

The variolins all contain a fused pyrido[3',2':4,5]pyrrolo[1,2-c]pyrimidine core (2), with either a heterocyclic aromatic ring or an ester group attached at C5, as in Variolin B (1) and Variolin D (3).

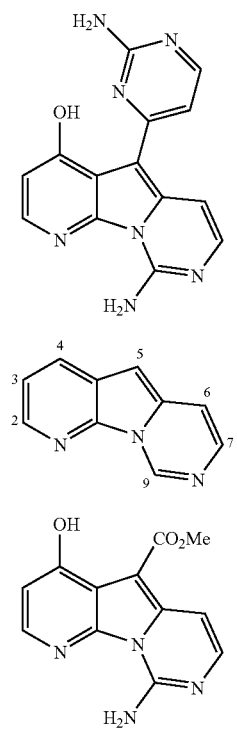

The variolins are disclosed to have antitumour activity and other useful properties. The complete structure, and antitumour activity, of these and related compounds is described by N. B. Perry et al. *Tetrahedron*, 1994, 50, 3987-92, and G. Trimurtulu et al, *Tetrahedron*, 1994, 50, 3993-4000. However, the variolins described in these documents have hitherto only been demonstrated to exhibit a limited range of antitumour activity.

The limited availability of natural material has resulted in the search for alternative synthetic methods being sought for the natural compounds and related analogs.

A synthetic process for producing the related deoxyvariolin B (4) has been described by M. Alvarez et al, *Tetrahedron Lett.*, 2001, 42, 315-317 (which was published before the filing date of the present application but after the priority dates).

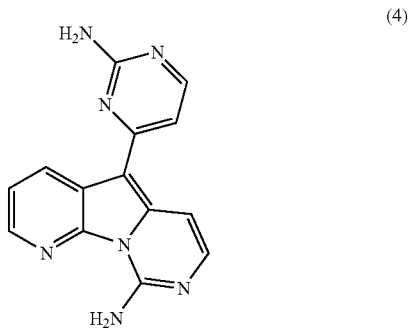

The route to deoxyvariolin B described in this reference involves a total of at least fourteen steps, in which the fused tricyclic pyridopyrrolopyrimidine core is constructed from a 7-azaindole and a heteroaryl coupling reaction is then used to introduce the fourth aromatic ring to give intermediate (5). Substitution of the derived sulphone group (6) for an amino group gave deoxyvariolin B (4):

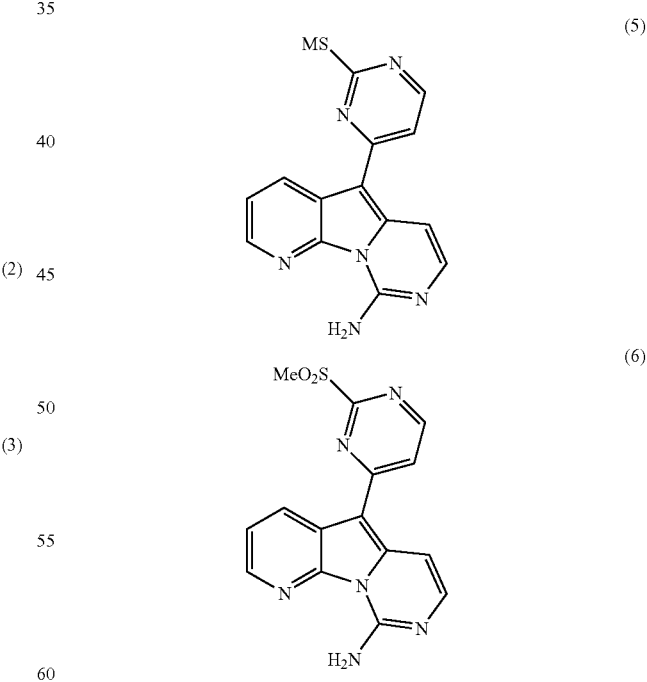

However, as noted above, this synthesis is long and complex. Further, no synthetic process has been reported for variolin B (or any of the natural variolins).

It is therefore desirable to provide a process capable of synthesising deoxyvariolin B and derivatives thereof in a smaller number of steps than the process described above.

It is also desirable to provide a process capable of synthesising variolin B itself as well as the deoxy derivative.

It is further desirable to provide new compounds having antitumour activity comparable or super nitrogen atom to which they are attached, may form a 5-14 membered heterocyclic ring;
the aryl group and the aryl moiety of the aralkyl and arylalkenyl group is a carbocyclic aryl group having from 6 to 14 carbon atoms in a carbocyclic ring or two or more fused rings;
the aralkyl group is a $C_1$-$C_6$ alkyl group which is substituted by an aryl group as defined above;
the arylalkenyl group is a $C_2$-$C_6$ alkenyl group which is substituted by an aryl group as defined above;
the heteroaromatic group is a heterocyclic aromatic group having from 5 to 14 ring atoms in one ring or two or more fused rings of which at least one ring atom is selected from the group consisting of nitrogen, oxygen and sulphur, and such a heterocyclic aromatic group fused with an aryl group as defined above;
the substituents on the aryl and heteroaromatic groups and the aryl moiety of the aralkyl and arylalkenyl groups are selected from the group consisting of $C_1$-$C_{12}$ alkyl, $C_1$-$C_{12}$ haloalkyl, $C_1$-$C_{12}$ alkoxy, $C_1$-$C_{12}$ alkylthio, $NH_2$, $C_1$-$C_4$ alkylamino, di($C_1$-$C_4$ alkyl)amino, $C_1$-$C_4$ alkanoylamino, di($C_1$-$C_4$ alkanoyl)amino, $NO_2$, CN and halogen;
and derivatives thereof where the nitrogen atom is quaternised,
and salts and esters thereof,
the process including the production of an intermediate of formula (II)

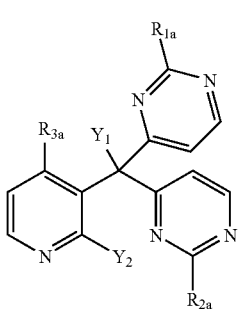

(II)

wherein:
$R_{1a}$, $R_{2a}$ and $R_{3a}$ represent any of the groups represented by $R_1$, $R_2$ and $R_3$ respectively, and all such groups where reactive functional groups are protected; and
$Y_1$ and $Y_2$ are groups capable of being eliminated to produce a fused tricyclic pyridopyrrolopyrimidine ring structure.

As described below, the new compounds of formula (I) demonstrate biological activity against mammalian cancer cell lines. Antitumoural activities of these compounds include leukaemias, lung cancer, colon cancer, kidney cancer, prostate cancer, ovarian cancer, breast cancer, sarcomas and melanomas. Further, the known compounds of formula (I) exhibit previously undisclosed activity against a wide range of cancers.

Thus, in a third aspect, the invention provides a method for the treatment or prophylaxis of cancer in a mammal, which comprises administering to a mammal in need of such treatment an effective amount of a new compound of the invention.

Further, in a fourth aspect, the invention provides a method for the treatment or prophylaxis of cancers selected from ovarian cancer, kidney cancer, prostate cancer, breast cancer and melanoma in a mammal, which comprises administering to a mammal in need of such treatment an effective amount of either a new compound of the invention or a variolin compound of the prior art.

In further aspects, the invention provides synthetic steps to certain preferred compounds, described in more detail later, and to intermediate compounds, especially those of formula (II) above.

DETAILED DESCRIPTION OF PREFERRED EMBODIMENTS

In the definitions used in the present application, alkyl groups may be straight or branched chain groups and preferably have from 1 to about 12 carbon atoms, more preferably 1 to about 8 carbon atoms, still more preferably 1 to about 6 carbon atoms, and most preferably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members.

Haloalkyl groups are alkyl groups (including cycloalkyl groups) as defined above which are substituted with one or more halogen atoms (preferably fluorine, chlorine, bromine or iodine) and preferably have from 1 to about 12 carbon atoms, more preferably 1 to about 8 carbon atoms, still more preferably 1 to about 6 carbon atoms, and most preferably 1, 2, 3 or 4 carbon atoms. Methyl, ethyl and propyl including isopropyl groups which are substituted with 1, 2 or 3 halogen atoms which may be the same or different, especially fluoromethyl, fluorochloromethyl, trifluoromethyl and trichloromethyl, are particularly preferred haloalkyl groups in the compounds of the present invention.

Preferred alkenyl and alkynyl groups in the compounds of the present invention have one or more unsaturated linkages and from 2 to about 12 carbon atoms, more preferably 2 to about 8 carbon atoms, still more preferably 2 to about 6 carbon atoms, even more prefereably 2, 3 or 4 carbon atoms. The terms alkenyl and alkynyl as used herein refer to both cyclic and noncyclic groups, although straight or branched noncyclic groups are generally more preferred.

Preferred alkoxy groups in the compounds of the present invention include groups having one or more (but preferably only one) oxygen linkages and from 1 to about 12 carbon atoms, more preferably from 1 to about 8 carbon atoms, and still more preferably 1 to about 6 carbon atoms, and most preferably 1, 2, 3 or 4 carbon atoms.

Preferred alkylthio groups in the compounds of the present invention have one or more (but preferably only one) thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred.

Preferred alkylsulfinyl groups in the compounds of the present invention include those groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2, 3 or 4 carbon atoms are particularly preferred.

Preferred alkylsulfonyl groups in the compounds of the present invention include those groups having one or more sulfonyl ($SO_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred.

Preferred alkanoyl groups in the compounds of the present invention include those groups having one or more carbonyl (CO) groups and from 1 to about 12 carbon atoms, more preferably from 1 to about 8 carbon atoms, and still more preferably 1 to about 6 carbon atoms (including the carbonyl carbon). Alkanoyl groups having 1, 2, 3 or 4 carbon atoms, especially the formyl, acetyl, propionyl, butyryl and isobutyryl groups, are particularly preferred.

Preferred alkylamino groups in the compounds of the present invention have one or more (but preferably only one) NH linkages and from 1 to about 12 carbon atoms, more preferably from 1 to about 8 carbon atoms, and still more preferably 1 to about 6 carbon atoms. Alkylamino groups having 1, 2, 3 or 4 carbon atoms, especially the methylamino, ethylamino, propylamino and butylamino groups, are particularly preferred.

Preferred dialkylamino groups in the compounds of the present invention have one or more (but preferably only one) nitrogen atom bonded to two alkyl groups, each of which may from 1 to about 12 carbon atoms, more preferably from 1 to about 8 carbon atoms, and still more preferably 1 to about 6 carbon atoms. The alkyl groups may be the same or different Dialkylamino groups wherein each alkyl group has 1, 2, 3 or 4 carbon atoms, especially the dimethylamino, diethylamino, N-methylethylamino, N-ethylpropylamino, dipropylamino, dibutylamino and N-methylbutylamino groups, are particularly preferred.

Preferred alkanoylamino groups in the compounds of the present invention have one NH—CO— linkage bonded to an alkyl group having from 1 to about 12 carbon atoms, more preferably from 1 to about 8 carbon atoms, and still more preferably 1 to about 6 carbon atoms. Alkanoylamino groups having 1, 2, 3 or 4 carbon atoms, especially the formylamino, acetylamino, propionylamino and butyrylamino groups, are particularly preferred. The acetylamino group is especially preferred.

Preferred dialkanoylamino groups in the compounds of the present invention have one nitrogen atom bonded to two alkanoyl groups as defined above, each of which may be the same or different and has from 1 to about 12 carbon atoms, more preferably from 1 to about 8 carbon atoms, and still more preferably 1 to about 6 carbon atoms. Dialkanoylamino groups wherein each alkanoyl group has 1, 2, 3 or 4 carbon atoms, especially the diformylamino, formylacetylamino, diacetylamino, dipropionylamino and dibutyrylamino groups, are particularly preferred. The diacetylamino group is especially preferred.

Preferred alkylsulfonylamino groups in the compounds of the present invention have one NH—SO$_2$— linkage bonded to an alkyl group having from 1 to about 12 carbon atoms, more preferably from 1 to about 8 carbon atoms, and still more preferably 1 to about 6 carbon atoms. Alkylsulfonylamino groups having 1, 2, 3 or 4 carbon atoms, especially the methanesulfonylamino, ethanesulfonylamino, propanesulfoylamino and butanesulfonylamino groups, are particularly preferred.

In the compounds of formula (I), $R_1$ is preferably selected from the group consisting of OH, OR', SH, SR', SOR', SO$_2$R', NH$_2$, NHR', N(R')$_2$, NHCOR', N(COR')$_2$, NHSO$_2$R', C(=O)R', CO$_2$H, CO$_2$R', $C_1$-$C_{12}$ alkyl and $C_1$-$C_{12}$ haloalkyl,
the or each group R' being independently selected from the group consisting of OH, $C_1$-$C_{12}$ alky, $C_1$-$C_{12}$ haloalkyl, aryl (which may optionally be substituted with a group selected from $C_1$-$C_6$ alkyl, $C_1$-$C_6$ alkoxy, $C_1$-$C_6$ alkylthio, NH$_2$, $C_1$-$C_6$ alkylamino, di($C_1$-$C_6$ alkyl)amino, NO$_2$, CN and halogen), aralkyl or arylalkenyl (the aryl moiety of which may optionally be substituted with a group selected from $C_1$-$C_6$ alkyl, $C_1$-$C_6$ alkoxy, $C_1$-$C_6$ alkylthio, NH$_2$, $C_1$-$C_6$ alkylamino, di($C_1$-$C_6$ alkyl)amino, NO$_2$, CN and halogen), and wherein the group $R_1$ is a group of formula N(R')$_2$ or N(COR')$_2$, each of the R' groups may be the same or different, or the two R' groups, together with the nitrogen atom to which they are attached, form a 5-12 membered heterocyclic ring.

More preferably, $R_1$ is selected from the group consisting of OR', SR', SOR', NH$_2$, NHR', N(R)$_2$, NHCOR', N(COR')$_2$ and NHSO$_2$R', the or each group R' being independently selected from the group consisting of $C_1$-$C_6$ alkyl, $C_1$-$C_6$ haloalkyl, aryl (which may optionally be substituted with a group selected from $C_1$-$C_6$ alkyl, $C_1$-$C_6$ alkoxy and halogen), aralkyl (the aryl moiety of which may optionally be substituted with a group selected from $C_1$-$C_6$ alkyl, $C_1$-$C_6$ alkoxy and halogen), aralkenyl (the aryl moiety of which may optionally be substituted with a group selected from $C_1$-$C_6$ alkyl, $C_1$-$C_6$ alkoxy and halogen), and wherein the group $R_1$ is a group of formula N(R')$_2$ or N(COR')$_2$, the two R' groups, together with the nitrogen atom to which they are attached, may form a 5-10 membered heterocyclic ring.

Even more preferably, $R_1$ is selected from the group consisting of $C_1$-$C_4$ alkoxy, $C_1$-$C_4$ alkylthio, $C_1$-$C_4$ alkylsulfinyl, amino, $C_1$-$C_4$ alkylamino, di($C_1$-$C_4$ alkyl)amino, $C_1$-$C_4$ alkanoylamino, di($C_1$-$C_4$ alkanoyl)amino, $C_1$-$C_4$ haloalkanoylamino, arylamino (wherein the aryl moiety may optionally be substituted with a $C_1$-$C_4$ alkoxy group), benzylamino (wherein the phenyl part of the benzyl moiety may optionally be substituted with a $C_1$-$C_4$ alkoxy group), cinnamoylamino or dicinnamoylamino (wherein the phenyl part of the or each cinammoyl moiety may optionally be substituted with a $C_1$-$C_4$ alkoxy group), or a 5- to 7-membered nitrogen-containing heterocyclic ring attached to the remainder of the molecule via its nitrogen atom.

Still more preferably, $R_1$ is selected from methoxy, thiomethyl, methylsulfinyl, amino, methylamino, ethylamino, benzylamino, acetylamino, trifluoroacetylamino, diacetylamino, cinnamoylamino, dicinnamoylamino, p-methoxybenzylamino and piperidino.

Most preferably $R_1$ is selected from amino, benzylamino, acetylamino, trifluoroacetylamino, diacetylamino, cinnamoylamino, dicinnamoylamino and p-methoxybenzylamino.

$R_2$ is preferably selected from the group consisting of OH, OR', SH, SR', SOR', SO$_2$R', NH$_2$, NHR', N(R')$_2$, NHCOR', N(COR')$_2$, NHSO$_2$R', C(=O)R', CO$_2$H, CO$_2$R', $C_1$-$C_{12}$ alkyl and $C_1$-$C_{12}$ haloalkyl,
the or each group R' being independently selected from the group consisting of OH, $C_1$-$C_{12}$ alkyl, $C_1$-$C_{12}$ haloalkyl, aryl (which may optionally be substituted with a group selected from $C_1$-$C_6$ alkyl, $C_1$-$C_6$ alkoxy, $C_1$-$C_6$ alkylthio, NH$_2$, $C_1$-$C_6$ alkylamino, di($C_1$-$C_6$ alkyl)amino, NO$_2$, CN and halogen), aralkyl or arylalkenyl (the aryl moiety of which may optionally be substituted with a group selected from $C_1$-$C_6$ alkyl, $C_1$-$C_6$ alkoxy, $C_1$-$C_6$ alkylthio, NH$_2$, $C_1$-$C_6$ alkylamino, di($C_1$-$C_6$ alkyl)amino, NO$_2$, CN and halogen), and wherein the group $R_2$ is a group of formula N(R')$_2$ or N(COR')$_2$, each of the R' groups may be the same or different, or the two R' groups, together with the nitrogen atom to which they are attached, form a 5-12 membered heterocyclic ring.

More preferably, $R_2$ is selected from the group consisting of OR', SR', SOR', NH$_2$, NHR, N(R')$_2$, NHCOR', N(COR')$_2$ and NHSO$_2$R', the or each group R' being independently selected from the group consisting of $C_1$-$C_6$ alkyl, $C_1$-$C_6$ haloalkyl, aryl (which may optionally be substituted with a group selected from $C_1$-$C_6$ alkyl, $C_1$-$C_6$ alkoxy and halogen), aralkyl (the aryl moiety of which may optionally be substituted with a group selected from $C_1$-$C_6$ alkyl, $C_1$-$C_6$ alkoxy and halogen), aralkenyl (the aryl moiety of which may optionally be substituted with a group selected from $C_1$-$C_6$ alkyl, $C_1$-$C_6$ alkoxy and halogen), and wherein the group $R_2$ is a group of formula $N(R')_2$ or $N(COR')_2$, the two R' groups, together with the nitrogen atom to which they are attached, may form a 5-10 membered heterocyclic ring.

Even more preferably, $R_2$ is selected from the group consisting of $C_1$-$C_4$ alkoxy, $C_1$-$C_4$ alkylthio, $C_1$-$C_4$ alkylsulfinyl, amino, $C_1$-$C_4$ alkylamino, di($C_1$-$C_4$ alkyl)amino, $C_1$-$C_4$ alkanoylamino, di($C_1$-$C_4$ alkanoyl)amino, $C_1$-$C_4$ haloalkanoylamino, arylamino (wherein the aryl moiety may optionally be substituted with a $C_1$-$C_4$ alkoxy group), benzylamino (wherein the phenyl part of the benzyl moiety may optionally be substituted with a $C_1$-$C_4$ alkoxy group), cinnamoylamino or dicinnamoylamino (wherein the phenyl part of the or each cinammoyl moiety may optionally be substituted with a $C_1$-$C_4$ alkoxy group), or a 5- to 7-membered nitrogen-containing heterocyclic ring attached to the remainder of the molecule via its nitrogen atom.

Yet more preferably, $R_2$ is selected from thiomethyl, methylsulfinyl, amino, methylamino, ethylamino, acetylamino, diacetylamino, cinnamoylamino, and p-methoxybenzylamino.

Most preferably, $R_2$ is selected from amino, acetylamino, diacetylamino and p-methoxybenzylamino.

Preferably, $R_3$ is H.

As the person skilled in the art will readily appreciate, the preferred definitions of $R_1$, $R_2$ and $R_3$ above may be combined in various ways, and the compounds covered by such combinations of the above preferred definitions are to be considered as being part of this invention. A combination of two of these definitions is preferred, and a combination of all three preferred definitions is especially preferred.

The following compounds are most preferred:
N'-bisacetyldeoxyvariolin;
N'-bisacetyl-N-acetyldeoxyvariolin;
N'-bisacetyl-N-bisacetyldeoxyvariolin;
N'-acetyldeoxyvariolin;
N'-acetyl-N-acetyldeoxyvariolin;
N'-biscinnamoyldeoxyvariolin;
N'-biscinnamoyl-N-cinnamoyldeoxyvariolin;
N'-methanesulfonyldeoxyvariolin;
N'-trifluoroacetyldeoxyvariolin;
2'-methoxydeoxyvatiolin;
2'-piperidinyldeoxyvariolin;
N'-ethyldeoxyvariolin;
N'-butyl-N'-methyldeoxyvariolin; and
N'-benzyldeoxyvariolin.

The compounds of formula (I) contain a basic group, and may therefore form a salt. The nature of such salts is not critical to the present invention, provided that, when the compound is used for therapeutic purposes, the salts are pharmaceutically acceptable, ie more biologically active, about as biologically active or not unduly less biologically active than the free base compound, and less toxic, about as toxic or not unduly more toxic than the free base compound. This can easily be ascertained by simple tests readily apparent to those skilled in the art. However, when the compound is used for other purposes (for example, as an intermediate in the preparation of another compound) even this restriction does not apply. Examples of suitable salts include inorganic acid salts such as hydrochloride, hydrobromide, sulfate and phosphate; organic acid salts such as acetate, benzoate, oxalate, maleate, fumarate, tartrate, citrate and succinate; and sulfonic acid salts such as methanesulfonate, benzenesulfonate and p-toluenesulfonate. Preferred salts include hydrochloride, hydrobromide, tartrate and succinate.

Some of the compounds of formula (I) contain a carboxy group, and may therefore form an ester. The nature of such esters is not critical to the present invention, provided that, when the compound is used for therapeutic purposes, the esters are pharmaceutically acceptable, ie more biologically active, about as biologically active or not unduly less biologically active than the free acid compound, and less toxic, about as toxic or not unduly more toxic than the free acid compound. It is preferred that the ester group is physiologically removable, ie the ester can be readily converted in vivo to the free acid. This can easily be ascertained by simple tests readily apparent to those skilled in the art.

The compounds of the present invention contain at least four tertiary amine groups, of which one or more (but preferably only one) may be quaternised to form a quaternary ammonium salt. In this case, a counter ion is also present; examples of suitable counter ions are defined above with reference to salts. The procedure for quaternising the nitrogen atom(s) is readily apparent to those skilled in the art. It is preferred that the group attached to the tertiary amino group to form a quaternary ammonium species is a $C_1$-$C_6$ alkyl group, most preferably a methyl group.

The variolin derivatives of formula (I), including the known variolin compounds, are produced by a novel process which forms part of the present invention.

An element of the process of the invention involves the formation of the intermediate of formula (II) below:

(II)

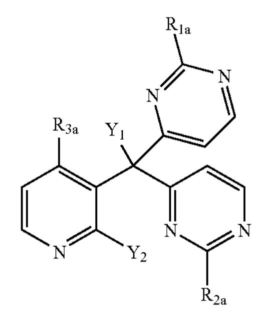

In the intermediate of formula (II), $R_{1a}$, $R_{2a}$ and $R_{3a}$ represent any of the groups represented by $R_1$, $R_2$ and $R_3$ respectively, and all such groups where reactive functional groups are protected; and $Y_1$ and $Y_2$ are groups capable of being eliminated to produce a fused tricyclic pyridopyrrolopyrimidine ring structure. The intermediates of formula (II) are novel compounds and also form part of the present invention.

Any protecting group known in the art may be used to form the groups $R_{1a}$, $R_{2a}$ and $R_{3a}$ with reactive functionalities protected. In this regard, reference is made to T. W. Greene et al, "Protective Groups in Organic Synthesis", John Wiley & Sons, 1991.

Any groups capable of being eliminated to produce a fused tricyclic pyridopyrrolo-pyrimidine ring structure may be used as the groups $Y_1$ and $Y_2$. Preferably the group Y, is a hydroxy group or a labile ester group such as acetate, methanesulfonate, p-toluenesulfonate or trifluoromethanesulfonate, more preferably a hydroxy group. Preferably the group $Y_2$ is a halogen atom, more preferably a chlorine atom.

It is preferred that the intermediate of formula (II) is symmetrical, ie $R_{1a}$ and $R_{2a}$ are the same: as described below, this allows the intermediate to be made by addition of two equivalents of reagent to a precursor; this in turn shortens the synthesis. More preferably, $R_{1a}$ and $R_{2a}$ are both methylthio groups.

The intermediate of formula (II) can be made by a number of methods. One preferred method is by reacting an intermediate compound of formula (IV):

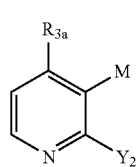
(IV)

wherein $R_{3a}$ and $Y_2$ are as defined above and M is a metal, with a compound of formula (V):

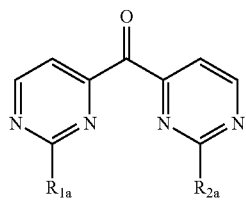
(V)

wherein $R_{1a}$ and $R_{2a}$ are as defined above.

In the compound of formula (IV) above, the nature of the metal atom M is not particularly critical, provided that the compound is sufficiently reactive to undergo addition to the compound of formula (V). Examples of suitable metallated species include those where M is Li, Na, K, Mg or Zn; in the case of metallated species with divalent metal ions, a further counterion such as halogen may also be present, or the compound may be in the form of a diorganometallic species. We prefer that M is Li.

The compound of formula (IV) is typically produced in situ by metallating the corresponding halo compound. Suitable reagents are well known in the art, and examples include the metal itself or another more active metallating compound such as an alkylmetal derivative. Alkyllithium derivatives are preferred and butyllithium is especially preferred.

The compound of formula (V) is preferably produced by reacting an intermediate compound of formula (VI):

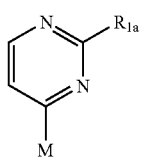
(VI)

wherein $R_{1a}$ is as defined above and M is a metal, with a compound of formula $L_1$-CO-$L_2$, where $L_1$ and $L_2$ are the same or different and each represents a leaving group.

In the compound of formula (VI), the nature of the metal atom M is not particularly critical, provided that the compound is sufficiently reactive to undergo addition to the compound of formula $L_1$-CO-$L_2$. Examples of suitable metallated species include those defined and exemplified above in relation to the compound of formula (IV). We prefer that M is Li.

The compound of formula (VI) is typically produced in situ by metallating the corresponding halo compound, ie a compound of formula (VIII):

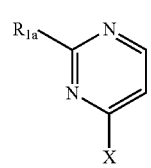
(VIII)

wherein $R_{1a}$ is as defined above and X is a halogen atom, preferably bromine or iodine.

The compound of formula (VIII) where $R_{1a}$ is methylthio and X is chloro is commercially available. Corresponding compounds where X is another halogen atom can be prepared from the corresponding chloro compound as described in the literature, see Majeed, A. J.; Antonsen. O.; Benneche, T.; Undheim, K. *Tetrahedron,* 1989, 45, 993 and Reference Example 1 below.

Suitable reagents and procedures for metallating the compound of formula (VIII) to produce the compound of formula (VI) are known in the art. Examples include the metal itself or another more active metallating compound such as an alkylmetal derivative. Alkyllithium derivatives are preferred and butyllithium is especially preferred.

In the compound of formula $L_1$-CO-$L_2$, $L_1$ and $L_2$ may be the same or different and each represents a leaving group, the precise nature of which is not especially critical. Non-limiting examples of suitable leaving groups include halogen, $C_1$-$C_6$ alkoxy, di($C_1$-$C_6$ alkyl)amino, nitrogen-containing heterocyclic (especially imidazole) or a labile ester group such as those defined above in relation to $Y_1$. Diethyl carbonate is a particularly preferred example of a compound of formula $L_1$-CO-$L_2$.

In an alternative preferred embodiment, the compound of formula (II) is produced by reacting an intermediate compound of formula (VI), described above, with an intermediate compound of formula (VII):

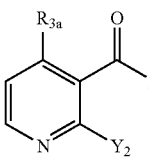
(VII)

wherein $R_{3a}$ and $Y_2$ are as defined above, and Z is a leaving group.

In the compound of formula (VI), the group Z is a leaving group, examples of which are defined above with reference to $Y_1$, $L_1$ and $L_2$. It is particularly preferred that Z is a halogen atom, especially chlorine, as two equivalents of the metallated compound of formula (VI) can add cleanly to the compound of formula (VII).

On elimination of the groups $Y_1$ and $Y_2$, the intermediate of formula (II) preferably cyclises to produce an intermediate of formula (III):

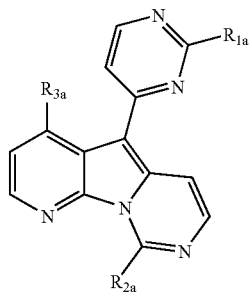
(III)

wherein $R_{1a}$, $R_{2a}$ and $R_{3a}$ are as defined above.

The elimination of the groups $Y_1$ and $Y_2$ is preferably carried out by reacting the intermediate of formula (II) with a trialkylsilane of formula $R_aR_bR_cSiH$ wherein $R_a$, $R_b$ and $R_c$ may be the same or different and each represents a $C_1$-$C_{12}$ alkyl group. Preferably triethylsilane is used as the reagent.

The reaction is preferably carried out in the presence of acid, the precise nature of which is not particularly critical. A strong organic acid such as p-toluenesulfonic acid or trifluoroacetic acid is preferred and trifluoroacetic acid is especially preferred.

The intermediate compound of formula (III) may then be converted to a compound of formula (I) by functional group interconversions, the general nature of which is known to those skilled in the art By way of example, the amine groups of the known compound deoxyvariolin B (4), prepared by the process of the present invention, may readily be converted into a variety of functionalised derivatives as shown in Scheme I and exemplified below.

Scheme I

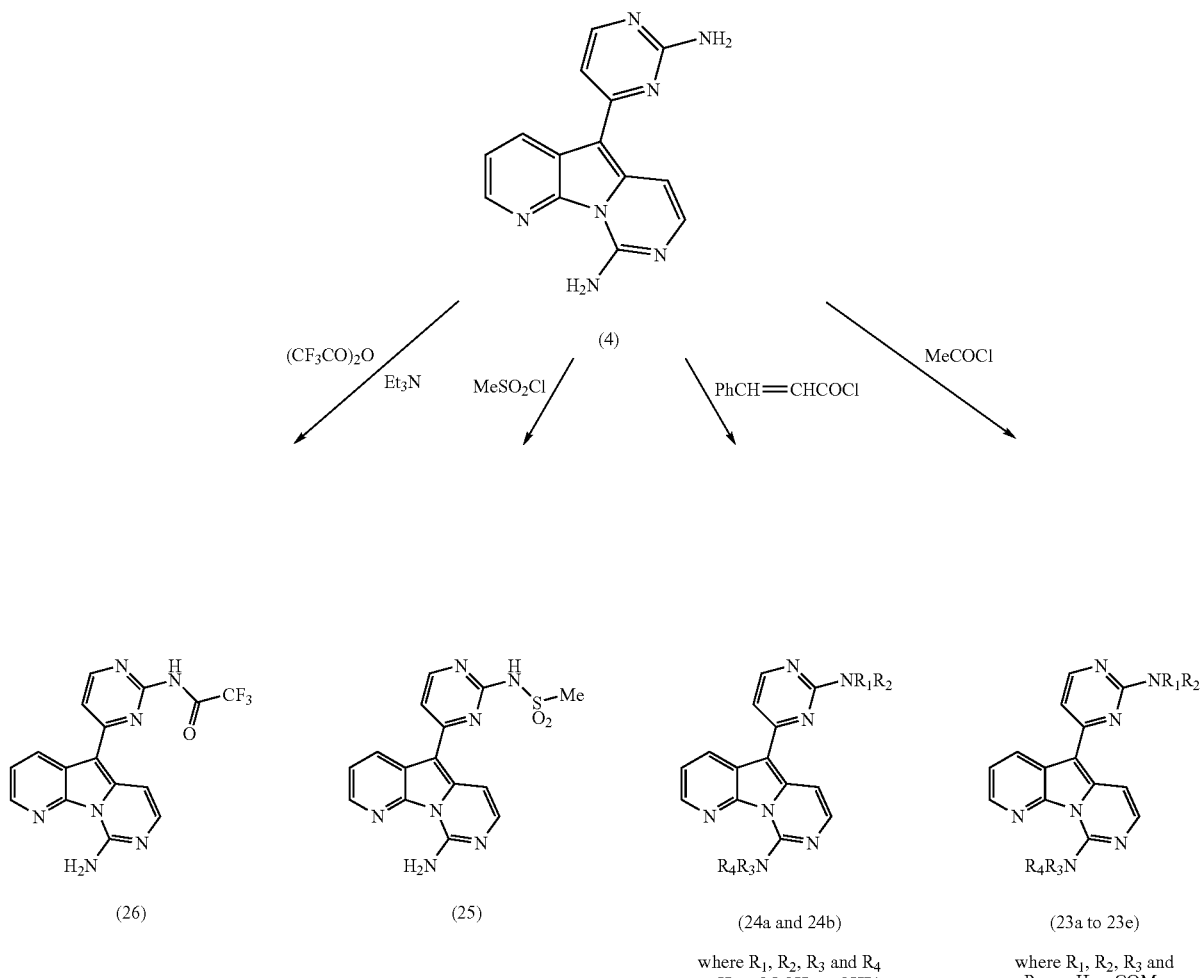

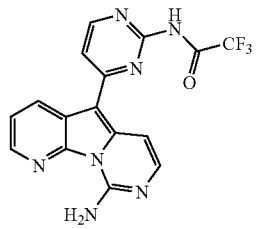
(26)

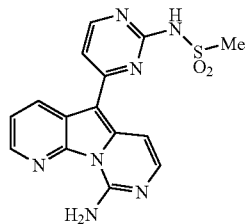
(25)

(24a and 24b)

where $R_1$, $R_2$, $R_3$ and $R_4$ are H or COCH=CHPh

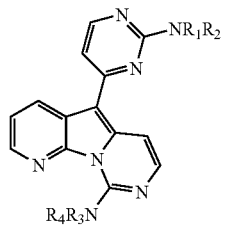
(23a to 23e)

where $R_1$, $R_2$, $R_3$ and $R_4$ are H or COMe

In an alternative approach, a further group of analogs may be generated by functionalisation of the C5 heteroaromatic ring of the variolins. This can be readily achieved from intermediate (5) by oxidation to the sulphone (6) or sulphoxide (22) followed by nucleophilic substitution reactions, as shown in Scheme II.

The nature of the amino-protecting group is not especially critical. Examples of suitable protecting groups, their attachment and their removal are given in T. W. Greene et al, "Protective Groups in Organic Synthesis", John Wiley & Sons, 1991, to which reference is made.

Scheme II 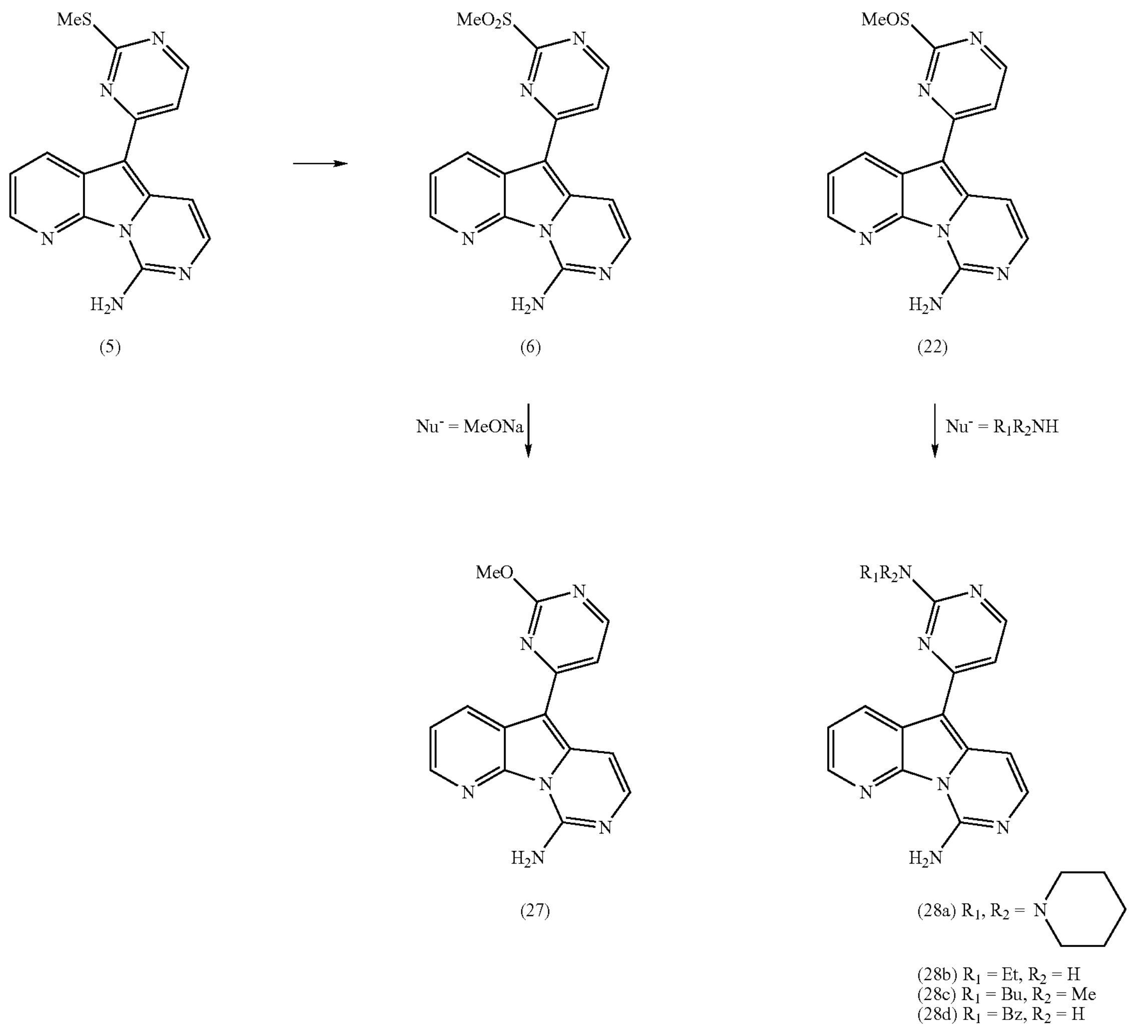 (5) (6) (22) (27)

Two particularly important interconversions have not previously been demonstrated for the variolins.

Therefore, in a further aspect, the invention provides a process for producing a compound of formula (I) wherein $R_1$ and $R_2$ are amino groups and $R_3$ is as defined above, said process comprising:

a) treating a compound of formula (I), wherein $R_{1a}$ and $R_{2a}$ are methylsulfinyl and $R_{3a}$ is as defined above, with a compound of formula $NH_2Prot$, where Prot is an amino-protecting group, to give a compound of formula (III), wherein $R_{1a}$ and $R_{2a}$ are protected amino and $R_{3a}$ is as defined above, and b) removing the amino-protecting group to give a compound of formula (I) wherein $R_1$ and $R_2$ are amino groups and $R_3$ is as defined above.

It is preferred that the protecting group is a substituted or unsubstituted benzyl group or a phthalimide group, especially a p-methoxybenzyl (PMB) group. The group may be removed by any conventional route, such as under acid conditions (especially a strong organic acid, for example trifluoromethanesulfonic acid or trifluoroacetic acid), under oxidising conditions, for example dichlorodicyanobenzoquinone (DDQ) or reductive conditions, for example with hydrogen and a palladium catalyst.

A preferred embodiment of such a process is illustrated in Scheme III below, in which the conversion of disulphoxide (20) into deoxyvariolin B (4) is achieved in two steps via the bis-amine (29).

Scheme III

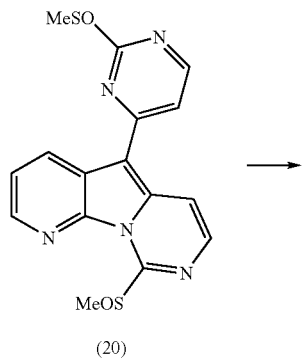

(20)

Scheme IV

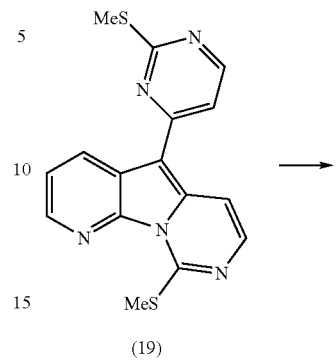

(19)

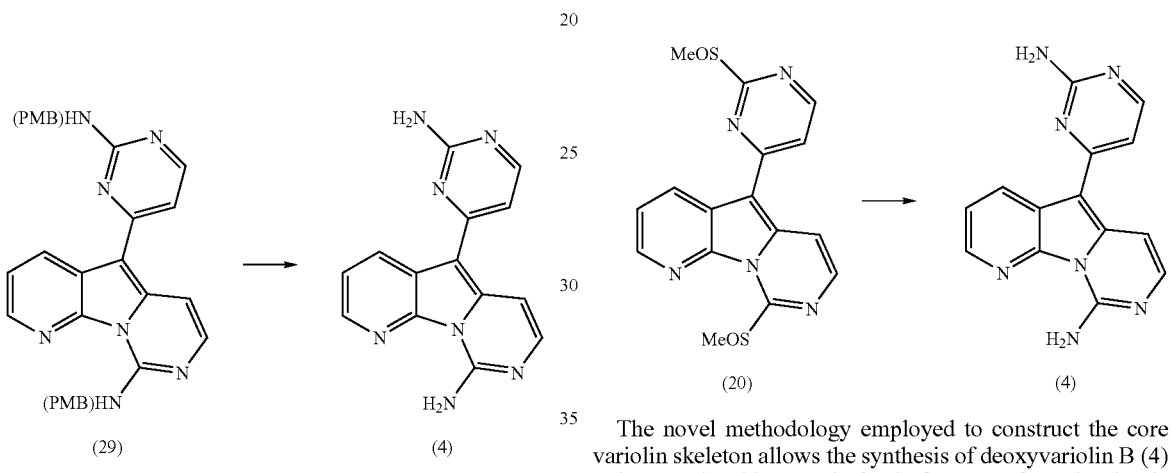

(29)　　(4)　　(20)　　(4)

The novel methodology employed to construct the core variolin skeleton allows the synthesis of deoxyvariolin B (4) to be completed in a total of only five steps from the simple monoheteroaromatic staring material (7). This synthesis is significantly shorter than the sequence to deoxyvariolin B described in the prior art.

In an alternative embodiment of such a process, illustrated in Scheme V below, dithioether intermediate (19) is converted into thiodeoxyvariolin (5) in a single step by treatment with ammonia solution:

In a yet further aspect, the invention provides a process for producing a compound of formula (I) wherein $R_1$ is a methylthio or amino group, $R_2$ is an amino group and $R_3$ is as defined in claim 1, from a compound of formula (III), wherein $R_{1a}$ and $R_{2a}$ are methylthio and $R_{3a}$ is as defined in claim 19, said process comprising:

a) optionally, oxidising the compound of formula ($R_1$) wherein $R_{1a}$, and $R_{2a}$ are methylthio to a compound of formula (III) wherein $R_{1a}$ and $R_{2a}$ are methylsulfinyl; and b) treating the compound of formula (III) wherein $R_{1a}$ and $R_{2a}$ are methylthio or methylsulfinyl with a reagent selected from sodium azide and ammonia Any oxidising agent capable of oxidising thioethers to sulfoxides may be used to achieve the optional oxidation step a) of the above process. Non-limiting examples of suitable oxidising agents include hydrogen peroxide, sodium periodate, t-BuOCl, sodium perborate, and peracids such as peracetic acid, m-chloroperbenzoic acid (mCPBA) or magnesium monoperoxyphthalate (MMPP), of which peracids are preferred and mCPBA is especially preferred.

An embodiment of such a process is illustrated in Scheme IV below, in which intermediate (19) is converted to deoxyvariolin B (4) in a single step via the sulfoxide intermediate (20):

Scheme V

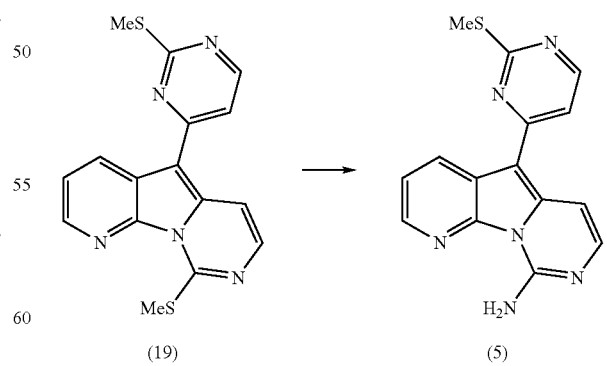

(19)　　(5)

A particularly preferred embodiment of the process of the present invention is illustrated in Scheme VI below. The precise conditions are described in more detail in the Examples, Process Examples and Reference Examples.

The novel synthetic approach of the present invention allows construction of the core variolin skeleton, consisting of the fused pyridopyrrolopyrimidine core bearing a heterocyclic aromatic ring at C5, as in (13), in only four steps from the simple monoheteroaromatic starting material (7).

Scheme VI 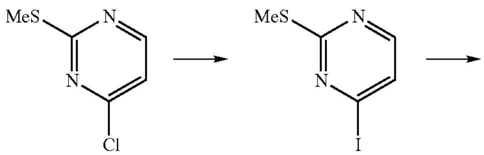 (7) (8)

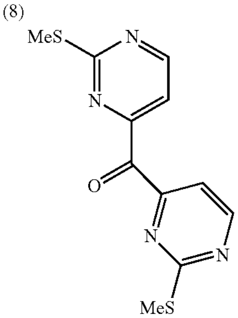

(9)

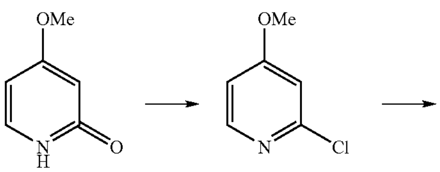

(10) (11)

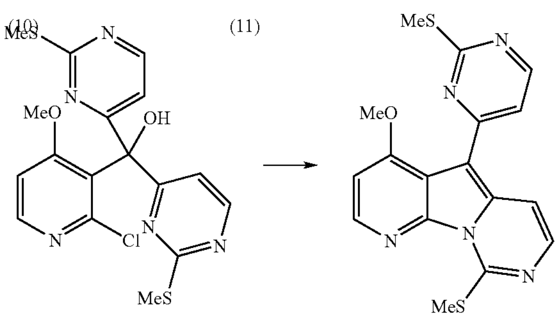

(12) (13)

Straightforward functional group manipulation then allows the conversion of intermediate (13) to the known compound variolin B (1) in four further steps, as illustrated in Scheme VII below:

Scheme VII 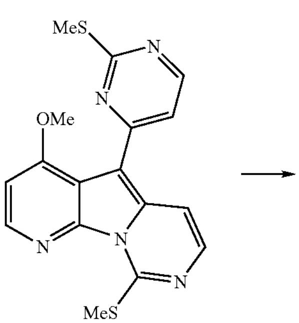 (13)

-continued 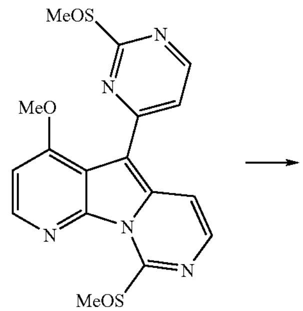 (14)

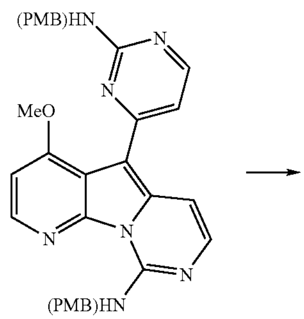

(15)

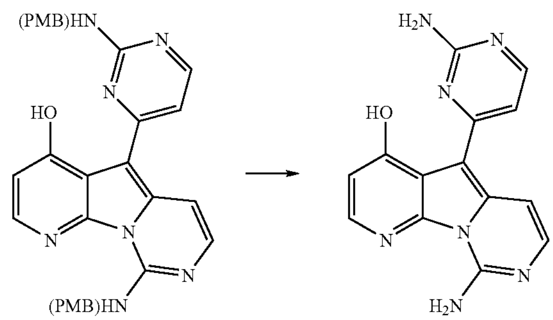

(16) (1)

This short eight step sequence from commercially available starting material (7) represents the first reported synthetic process for the preparation of variolin B.

Similar methodology provides rapid access to the key intermediate (19) useful for the synthesis of deoxy variolin B and related analogs, as illustrated in Scheme VIII below and described in more detail in the Examples, Process Examples and Reference Examples.

Scheme VIII 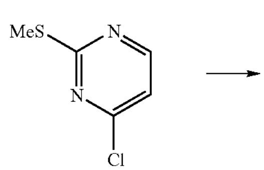 (7)

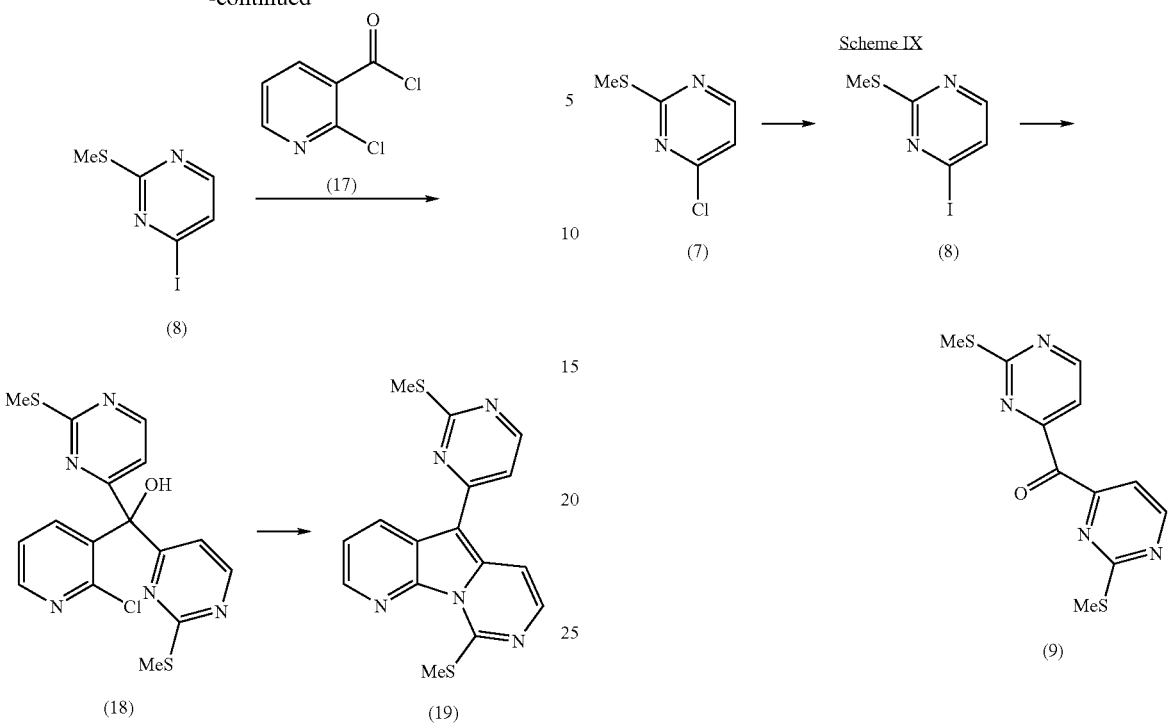
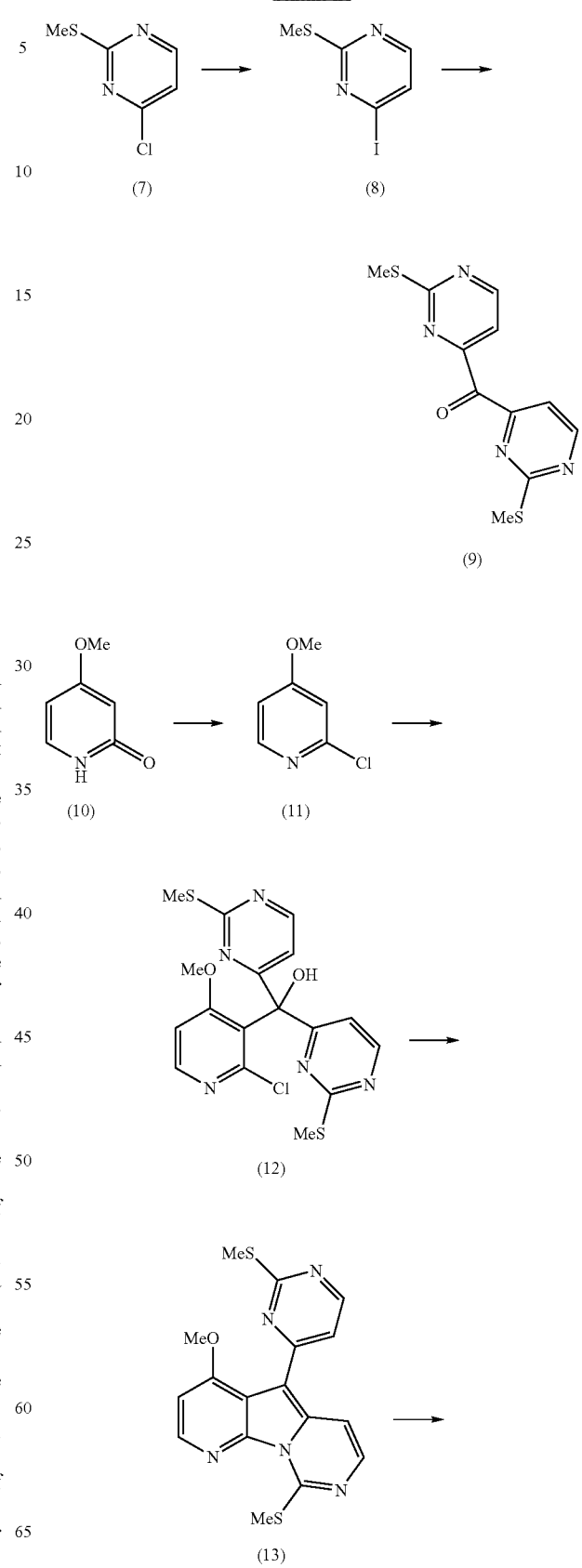

-continued (17)

(8)

(18)

(19)

The routes described above to variolin B or deoxyvariolin B can be conveniently modified to form other derivatives. In particular, this invention provides new compounds that can be made from intermediates prepared by a new process that is part of this invention.

Thus, according to the present invention, we now provide synthetic routes for the production of variolin B (1), deoxyvariolin B (4) and related intermediates such as (5) and thus for the production of variolin analogs. The synthetic routes of the invention each comprise a number of transformation steps to arrive at the desired product. Each step in itself is a process in accordance with this invention. The invention is not limited to the routes that are exemplified, and alternative routes may be provided by, for example, changing the order of the transformation steps, as appropriate.

In more detail, the synthesis of variolin B according to an especially preferred embodiment of the current invention involves the following eight steps.

(a) conversion of commercially available 4-chloro-2-thiomethylpyrimidine (7) to the iodo compound (8), (b) reaction of (8) with diethyl carbonate to give the symmetric ketone (9), (c) addition of (9) to a solution of the lithiated form of pyridine derivative (1) to form the triaryl alcohol (12), (d) tandem deoxygenation and cyclization of the triaryl alcohol (12) using a combination of triethylsilane and trifluoroacetic acid, (e) oxidation of intermediate (13) with mCPBA to the disulphoxide (14), (f) treatment of (14) with p-methoxybenzylamine to give the bis-amine (15), (g) conversion of the methoxy group of (15) to the alcohol (16) using sodium ethanethiolate, (h) removal of the p-methoxybenzyl protecting groups of (16) with triflic acid to give variolin B (1).

This synthesis is illustrated in Scheme IX below. Further details of the processes used are given in the Examples, Process Examples and Reference Examples.

Scheme IX (7) (8)

(9)

(10) (11)

(12)

(13)

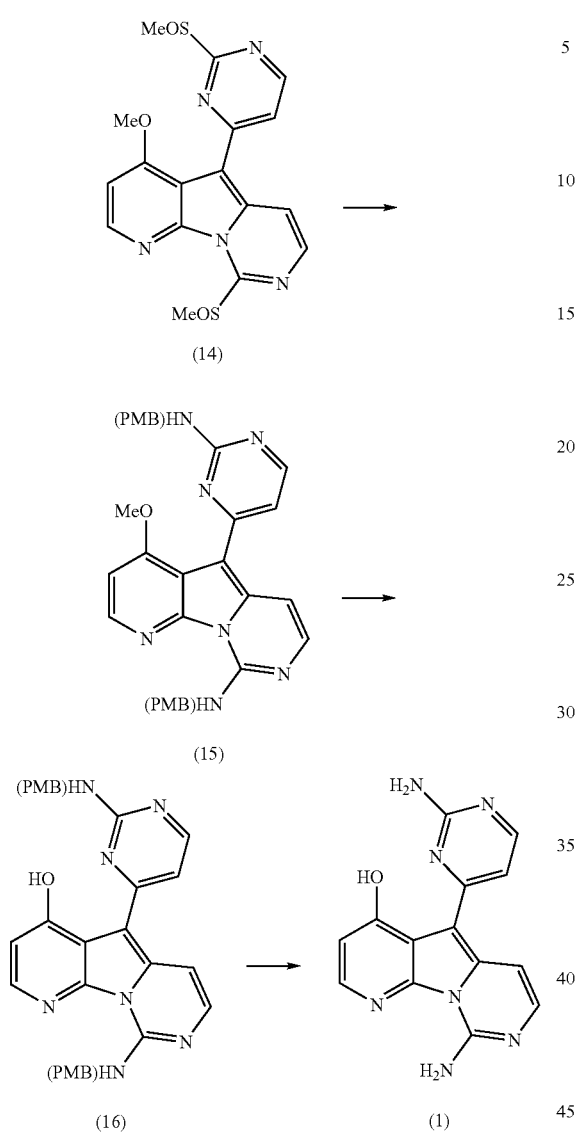

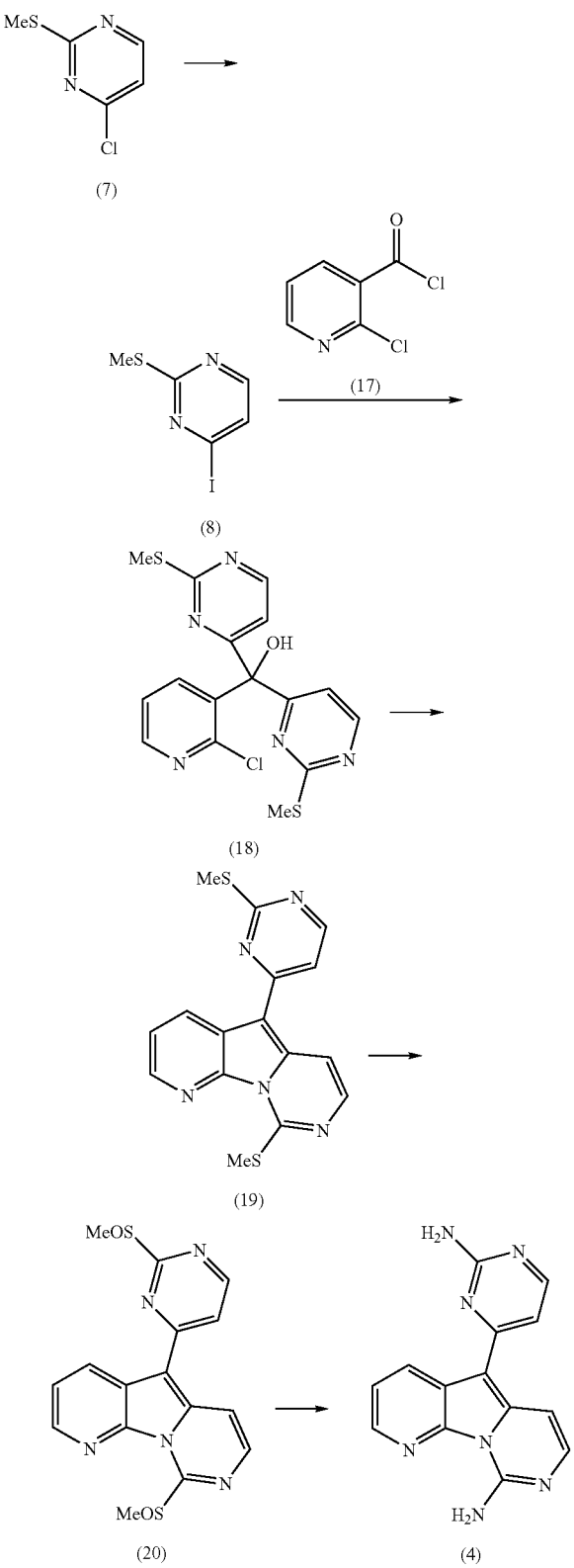

In another preferred modification, starting material (7) is transformed into deoxyvariolin B involving the following five further steps.

(a) conversion of commercially available 4-chloro-2-thiomethylpyrimidine (7) to the iodo compound (8),
(b) reaction of (8) with the pyridine derivative (17) to give the triaryl alcohol (18),
(c) tandem deoxygenation and cyclization of the triaryl alcohol (18) using a combination of triethylsilane and trifluoroacetic acid,
(d) oxidation with mCPBA of dithioether (19) to the disulphoxide (20),
(e) treatment of (20) with ammonia solution to give deoxyvariolin B (4).

This synthesis is illustrated in Scheme X below. Further details of the processes used are given in the Examples, Process Examples and Reference Examples.

As the skilled artisan will readily appreciate, the reaction schemes described herein may be modified and/or combined in various ways, and the compounds generated therefore are to be considered as being part of this invention. In particular the starting material and/or reagents and reactions can be varied to suit other combinations of the substituent groups in the formulae (I) to (VIII).

Pharmaceutical Compositions

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

Administration of the compounds or compositions of the present invention may be by any suitable method, such as intravenous infusion, oral preparations, intraperitoneal and intravenous administration.

Cytotoxic Activity

The compounds of the present invention were tested according to the protocol described below.

A colorimetric type of assay, using sulforhodamine B (SRB) reaction has been adapted for a quantitative measurement of cell growth and viability: see Skehan, P. A. et al. *J. Natl. Cancer Inst.*, 1990, 82, 1107-1112. This form of the assay employs 96 well cell culture microplates of 9 mm diameter (Faircloth, G. T.; Stewart, D. and Clement, J. J., *Journal of Tissue and Culture Methods*, 1983, 11, 201-205; Mosmann, T. *Journal of Immunological Methods*, 1983, 65, 55-63.).

Most of the cell lines are obtained from American Type Culture Collection (ATCC) derived from different human cancer types. Cells are maintained in RPMI 1640 10% FBS, supplemented with 0.1 g/l penicillin and 0.1 g/l streptomycin sulfate and then incubated at 37° C., 5% $CO_2$ and 98% humidity. For the experiments, cells were harvested from subconfluent cultures using trypsin and resuspended in fresh medium before plating.

Cells are seeded in 96 well microtiter plates, at 5×103 cells per well in aliquots of 195 µl medium, and they are allowed to attach to the plate surface by growing in drug free medium for 18 hours. Afterward, samples are in aliquots of 5 pi in a ranging from 10 to 10-8 µg/ml dissolved in DMSO/EtOH (0.2% in PS buffer). After 48 hours exposure, the antitumour effect are measured by the SRB methodology: cells are fixed by adding 50 µl of cold 50% (w/v) trichloroacetic acid (TCA) and incubating for 60 minutes at 4° C. Plates are washed with deionized water and dried. 100 µl of SRB solution (0.4% w/v in 1% acetic acid) is added to each microtiter well and incubated for 10 minutes at room temperature. Unbound SRB is removed by washing with 1% acetic acid. Plates are air-dried and bound stain is solubilized with Tris buffer. Optical densities are read on an automated spectrophotometric plate reader at a single wavelength of 490 nm.

The values for mean +/− SD of data from triplicate wells are calculated Some parameters for cellular responses can be calculated: TGI=growth inhibition, TGI=total growth inhibition (cytostatic effect) and LC=cell killing (cytotoxic effect).

The results are shown in Tables 1 and 2 below. Although compounds (1), (4), (5) and (6) are not themselves part of the present invention, the results disclosed in the Tables demonstrate antitumour activity not previously disclosed for these compounds.

This application claims priority from GB application nos. 0017055.5, filed 11 Jul. 2000, and 0030689.4, filed 15 Dec. 2000. The contents of both documents are hereby incorporated by reference to the extent that there is disclosure therein which is not explicitly reproduced in the present specification.

TABLE 1

Antitumour in vitro data

| COMPOUND | Cell line: | Tumor Type: | | | |
|---|---|---|---|---|---|
| | | NSCL | Colon | Melanoma | |
| | | A-549 | HT-29 | SW-620 | MEL-28 |
| Variolin B 1 | GI50 (M): | 7.E−07 | 7.E−07 | 1.E−07 | 7.E−07 |
| (Natural origin) | TGI (M): | 1.E−06 | 1.E−06 | 3.E−07 | 1.E−06 |
| | LC50 (M): | 3.E−06 | 3.E−06 | 2.E−06 | 2.E−06 |
| Deoxyvariolin 4 | GI50 (M): | 1.E−07 | 7.E−08 | 7.E−08 | 7.E−08 |
| | TGI (M): | 2.E−07 | 2.E−07 | 3.E−07 | 1.E−07 |
| | LC50 (M): | 4.E−07 | 1.E−05 | 1.E−05 | 3.E−07 |
| Thiodeoxyvariolin 5 | GI50 (M): | 1.E−06 | 6.E−07 | 3.E−06 | 6.E−08 |
| | TGI (M): | 3.E−06 | 2.E−06 | 1.E−05 | 3.E−07 |
| | LC50 (M): | 1.E−05 | 1.E−05 | 3.E−05 | 6.E−06 |

| COMPOUND | Cell line: | Tumor Type: | | | | |
|---|---|---|---|---|---|---|
| | | Ovary | Kidney | Prostate | Breast | |
| | | OVCAR-3 | A498 | DU-145 | MCF-7 | MB-231 |
| Variolin B 1 | GI50 (M): | | 1.E−07 | 1.E−07 | 7.E−07 | 3.E−07 |
| (Natural origin) | TGI (M): | | 3.E−07 | 3.E−07 | 2.E−06 | 1.E−06 |
| | LC50 (M): | | 2.E−06 | 1.E−06 | 2.E−06 | 3.E−06 |
| Deoxyvariolin 4 | GI50 (M): | 1.E−07 | 7.E−08 | 1.E−07 | 1.E−07 | 7.E−08 |
| | TGI (M): | 3.E−07 | 2.E−07 | 3.E−07 | 3.E−07 | 3.E−07 |
| | LC50 (M): | 4.E−07 | 7.E−07 | 7.E−06 | 4.E−06 | 3.E−05 |

TABLE 1-continued

Antitumour in vitro data

| Thiodeoxyvariolin 5 | GI50 (M): | 1.E−06 | 6.E−07 | 3.E−07 | 2.E−06 | 2.E−06 |
|---|---|---|---|---|---|---|
| | TGI (M): | 2.E−06 | 2.E−06 | 1.E−06 | 6.E−06 | 6.E−07 |
| | LC50 (M): | 3.E−06 | 3.E−06 | 3.E−06 | 3.E−05 | 1.E−05 |

GI50 50% growth inhibition
TGI Total growth inhibition (cytostatic effect)
LC50 50% net cell killing (cytotoxic effect)

TABLE 2

| | | | | | Antitumour in vitro data (M) | | | | | |
|---|---|---|---|---|---|---|---|---|---|---|
| Cpd | | | | | A-549 | | | HT-29 | | |
| No | MW | $R_1$ | $R_2$ | $R_3$ | GI50 | TGI | LC50 | GI50 | TGI | LC50 |
| 19 | 339.4 | SMe | SMe | H | $5.9\ 10^{-6}$ | $1.2\ 10^{-5}$ | $2.9\ 10^{-5}$ | $5.9\ 10^{-6}$ | $1.5\ 10^{-5}$ | $2.9\ 10^{-5}$ |
| 20 | 371.4 | SOMe | SOMe | H | $5.4\ 10^{-5}$ | $>1.3\ 10^{-4}$ | $>1.3\ 10^{-4}$ | $1.1\ 10^{-4}$ | $>1.3\ 10^{-4}$ | $>1.3\ 10^{-4}$ |
| 22 | 324.0 | SOMe | $NH_2$ | H | $1.2\ 10^{-6}$ | $6.2\ 10^{-6}$ | $9.2\ 10^{-5}$ | $9.2\ 10^{-7}$ | $1.5\ 10^{-5}$ | $>1.5\ 10^{-4}$ |
| 23a | 361.4 | $N(Ac)_2$ | $NH_2$ | H | $2.8\ 10^{-7}$ | $1.4\ 10^{-6}$ | $2.8\ 10^{-6}$ | $1.4\ 10^{-7}$ | $2.8\ 10^{-7}$ | $2.8\ 10^{-6}$ |
| 23b | 403.4 | $N(Ac)_2$ | NHAc | H | $7.4\ 10^{-7}$ | $2.0\ 10^{-6}$ | $7.4\ 10^{-6}$ | $1.0\ 10^{-7}$ | $1.7\ 10^{-6}$ | $2.5\ 10^{-6}$ |
| 23c | 445.4 | $N(Ac)_2$ | $N(Ac)_2$ | H | $2.2\ 10^{-6}$ | $1.3\ 10^{-5}$ | $2.2\ 10^{-5}$ | $1.1\ 10^{-6}$ | $2.0\ 10^{-6}$ | $1.8\ 10^{-5}$ |
| 23d | 319.3 | NHAc | $NH_2$ | H | $6.3\ 10^{-7}$ | $1.6\ 10^{-6}$ | $3.2\ 10^{-6}$ | $6.3\ 10^{-7}$ | $1.6\ 10^{-6}$ | $3.2\ 10^{-6}$ |
| 23e | 361.4 | NHAc | NHAc | H | $2.2\ 10^{-6}$ | $5.5\ 10^{-6}$ | $2.8\ 10^{-5}$ | $5.5\ 10^{-6}$ | $>2.8\ 10^{-5}$ | $>2.8\ 10^{-5}$ |
| 24a | 407.4 | $N(cinnamyl)_2$ | $NH_2$ | H | $1.2\ 10^{-7}$ | $1.2\ 10^{-6}$ | $1.2\ 10^{-5}$ | $4.9\ 10^{-6}$ | $1.2\ 10^{-5}$ | $>1.2\ 10^{-4}$ |
| 24b | 667.7 | $N(cinnamyl)_2$ | NHcinnamyl | H | $3.0\ 10^{-6}$ | $7.5\ 10^{-6}$ | $7.5\ 10^{-5}$ | $1.5\ 10^{-6}$ | $1.5\ 10^{-5}$ | $7.5\ 10^{-5}$ |
| 26 | 373.3 | $NHCOCF_3$ | $NH_2$ | H | $2.7\ 10^{-7}$ | $1.3\ 10^{-6}$ | $2.7\ 10^{-5}$ | $8.0\ 10^{-7}$ | $1.3\ 10^{-5}$ | $1.1\ 10^{-4}$ |
| 27 | 292.3 | OMe | $NH_2$ | H | $6.8\ 10^{-8}$ | $3.4\ 10^{-7}$ | $2.7\ 10^{-6}$ | $1.7\ 10^{-7}$ | $3.4\ 10^{-7}$ | $3.4\ 10^{-5}$ |
| 28d | 367.4 | NHBn | $NH_2$ | H | $1.4\ 10^{-6}$ | $2.7\ 10^{-6}$ | $2.7\ 10^{-5}$ | $1.4\ 10^{-6}$ | $2.4\ 10^{-6}$ | $2.2\ 10^{-5}$ |
| 28b | 305.3 | NHEt | $NH_2$ | H | $>3.3\ 10^{-5}$ | $>3.3\ 10^{-5}$ | $>3.3\ 10^{-5}$ | $>3.3\ 10^{-5}$ | $>3.3\ 10^{-5}$ | $>3.3\ 10^{-5}$ |
| 28a | 345.4 | Piperidinyl | $NH_2$ | H | $8.7\ 10^{-6}$ | $2.3\ 10^{-5}$ | $>2.9\ 10^{-5}$ | $5.8\ 10^{-6}$ | $2.0\ 10^{-5}$ | $>2.9\ 10^{-5}$ |
| 28c | 347.42 | NMeBu | $NH_2$ | H | $2.9\ 10^{-6}$ | $8.7\ 10^{-6}$ | $2.3\ 10^{-5}$ | $2.9\ 10^{-6}$ | $8.7\ 10^{-6}$ | $2.3\ 10^{-5}$ |
| 29 | 517.6 | NHPMB | NHPMB | H | $>9.7\ 10^{-5}$ | $>9.7\ 10^{-5}$ | $>9.7\ 10^{-5}$ | $>9.7\ 10^{-5}$ | $>9.7\ 10^{-5}$ | $>9.7\ 10^{-5}$ |
| 1 | 293.3 | $NH_2$ | $NH_2$ | OH | $1.7\ 10^{-7}$ | $6.8\ 10^{-7}$ | $1.7\ 10^{-4}$ | $1.0\ 10^{-6}$ | $1.7\ 10^{-5}$ | $>1.7\ 10^{-4}$ |
| 6 | 340.4 | $SO_2Me$ | $NH_2$ | H | $4.4\ 10^{-6}$ | $1.5\ 10^{-4}$ | $>1.5\ 10^{-4}$ | $2.9\ 10^{-5}$ | $1.5\ 10^{-4}$ | $>1.5\ 10^{-4}$ |

EXAMPLES

Processes for producing the compounds and intermediates of the present invention are described in the Examples below. In the Process Examples are described processes according to the present invention for producing known compounds. The production of intermediate compounds not part of the present invention is described in the Reference Examples.

General Experimental Details

Unless otherwise stated, all reactions were performed under an inert atmosphere in pre-dried glassware. All organic extracts were washed with water and brine, and dried over $MgSO_4$ prior to concentration in vacuo. Melting points were determined on a Kofler hot-stage apparatus and are uncorrected.

Example 1

Compound 13

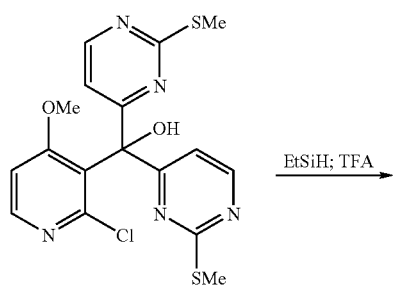

12

EtSiH; TFA →

-continued

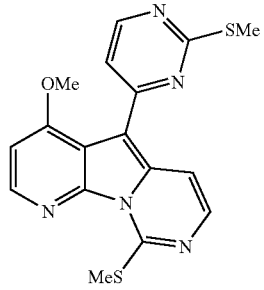

13

A mixture of triaryl alcohol 12 (100 mg, 0.237 mmol) (prepared as described in Example 16 below) and trifluoroacetic acid (37 μL, 0.48 mmol) were dissolved in 1,2-dichloroethane (0.5 mL). The resulting orange solution was transferred to a Young's tube fitted with a rubber septum, containing triethylsilane (0.30 mL, 1.9 mmol). Under a strong flow of argon, the septum was replaced with a Teflon® screw-cap, and the sealed reaction vessel was heated at 100° C. for 43 h. After cooling, the vessel was opened and the contents diluted with $CH_2Cl_2$ (12 mL). The solution was neutralised with 5% $NaHCO_3$ solution (8 mL) and the phases separated. The aqueous layer was repeatedly extracted with $CH_2Cl_2$ and the organic extracts were worked up according to *the standard procedure. Purification of the crude material was achieved by flash chromatography on silica gel using gradient elution (48 to 75% EtOAc/hexanes) to afford in order of elution:

(1) the variolin core structure 13 as a yellow solid (41 mg, 47%):

Mp: 192-194° C.; $^1$H NMR (500 MHz, CDCl$_3$): δ 2.65 (s, 3H), 2.70 (s, 3H), 6.92 (d, J=5.4 Hz, 1H), 7.40 (d, J=5.4 Hz, 1H), 7.71 (d, J=6.8 Hz, 1H), 7.98 (d, J=6.8 Hz, 1H), 8.48 (m, 2H); $^{13}$C NMR (75 MHz, CDCl$_3$): δ 14.1, 14.9, 55.6, 101.9, 102.5, 108.5, 110.8, 117.7, 135.9, 138.6, 143.5, 144.3, 154.2, 155.6, 159.6, 161.1, 171.2; HRMS: Calcd for C$_{17}$H$_{15}$N$_5$O$^{32}$S$_2$ (M$^+$) 369.0718, found 369.0720.

and (2) the uncyclised ether 13a as a viscous gum (28 mg, 28%)

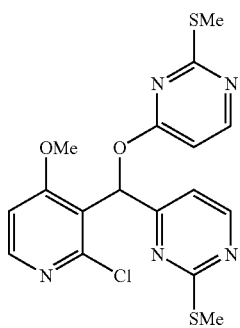

13a $^1$H NMR (500 MHz, CDCl$_3$): δ 2.36 (s, 3H), 2.44 (s, 3H), 3.84 (s, 3H) 6.57 (d, J=5.9 Hz, 1H), 6.80 (d, J=5.9 Hz, 1H), 7.17 (d, J=4.9 Hz, 1H), 7.79 (s, 1H), 8.27 (d, J=5.9 Hz, 1H), 8.30 (d, J=5.9 Hz, 1H), 8.49 (d, J=4.9 Hz, 1H); $^{13}$C NMR (75 MHz, CDCl$_3$): δ 14.0 (×2), 56.2, 71.8, 103.5, 106.4, 112.9, 120.8, 150.7, 152.5, 157.1, 158.0, 166.0, 167.1, 167.3, 172.1, 172.4; HRMS: Calcd for C$_{17}$H$_{16}$$^{35}$ClN$_5$O$_2$$^{32}$S$_2$ (M$^+$) 421.0434, found 421.0444.

Example 2

Compounds 14 and 15

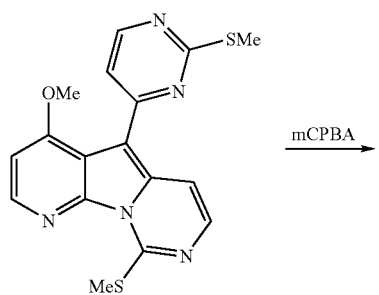

13

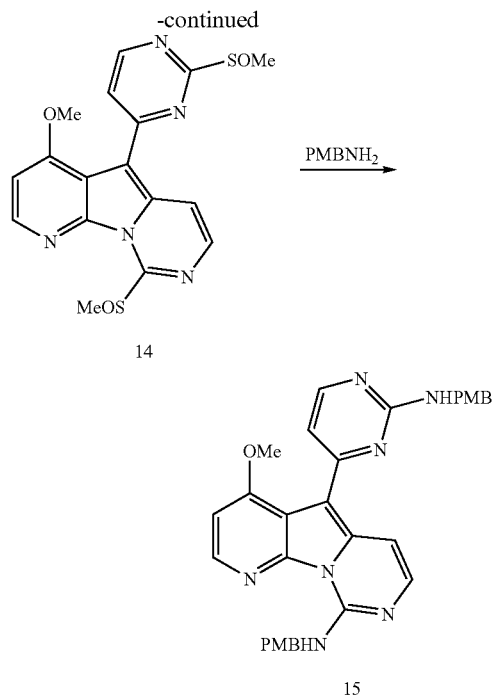

Bis-sulfide 13 (37 mg, 0.10 mmol) was dissolved in CHCl$_3$ (5 mL) under atmospheric conditions and cooled in a 40° C. bath. A pre-cooled (−40° C.) solution of m-chloroperbenzoic acid in CHCl$_3$ (10 mg/mL) was added dropwise to the solution until TLC analysis indicated the complete consumption of starting material (approx. 2 equiv of m-CPBA was used). The solution was warmed to room temperature and neutralised with saturated NaHCO$_3$ solution. This was repeatedly extracted with CH$_2$Cl$_2$ and after the standard work-up, a yellow solid was obtained, which was predominantly a mixture of diastereomeric bis-sulfoxides. The crude mixture was used without purification, however the bis-sulfoxides 14 had the following spectroscopic characteristics:

$^1$H NMR (500 MHz, CDCl$_3$): (most signals for the diastereoisomers coincide, however, as they represent more than one compound they are all quoted as multiplets) δ 3.02 (m, 3H), 3.19 (m, 3H), 4.12 (m, 3H), 7.00-7.01 (m, 1H), 7.98-7.99 (m, 1H), 8.12-8.14 (m, 1H), 8.48-8.49 (m, 1H), 8.64-8.67 (m, 1H), 8.79-8.81 (m, 1H).

The crude oxidised material was heated with an excess of p-methoxybenzylamine (0.15 mL, 1.1 mmol) at 85° C. for 15 h. The crude red paste was purified by flash chromatography on silica gel using gradient elution (2.5-4% MeOH/CH$_2$Cl$_2$). The yellow fractions were re-chromatographed using gradient elution (50% EtOAc/CH$_2$Cl$_2$ to 100% EtOAc) to give bis-amine 15 as a yellow solid (43 mg, 78% over two steps).

Mp: 74-77° C.; $^1$H NMR (500 MHz, CDCl$_3$): δ 3.81 (s, 6H), 3.99 (s, 3H), 4 5.6 Hz, 2H), 4.85 (d, J=5.5 Hz, 2H), 5.51 (m, 1H), 6.82 (d, J=5.6 Hz, 1H), 6.89-6.91 (m, 4H), 7.00 (d, J=5.2 Hz, 1H), 7.29 (m, 1H), 7.34 (d, J=8.5 Hz, 2H), 7.39 (d, J=8.5 Hz, 2H), 7.43 (m, 1H), 8.16 (d, J=5.6 Hz, 1H), 8.26 (d, J=5.2 Hz, 1H), 10.39 (m, 1H); $^{13}$C NMR (75 MHz, CDCl$_3$): δ 44.3, 44.9, 55.3 (2×CH$_3$), 55.5, 101.3, 101.6, 101.8, 111.4, 112.2, 114.0 (×2), 128.5, 128.8, 130.5, 131.4, 137.5, 141.5, 141.9, 144.7, 148.7, 154.6 (br), 158.7, 158.9, 159.4, 160.9, 162.6; HRMS: Calcd for C$_{31}$H$_{29}$N$_7$O$_3$ (M$^+$) 547.2332, found 547.2334.

Example 3

Compound 16

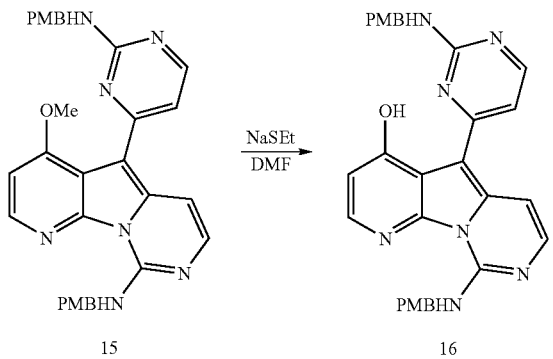

NaH (60%, 60 mg, 1.5 mmol) was washed three times with petroleum ether, and suspended in dry DMF (1.5 mL). The stirred suspension was cooled in ice, and ethanethiol (0.14 mL, 1.9 mmol) was added dropwise. After the gas evolution had subsided, the clear solution was stirred at room temperature for 10 min. A portion of the NaSEt solution (1.1 mL) was added to a solution of bis-amine 15 (40 mg, 0.073 mmol) in dry DMF (1.5 mL) and the mixture was stirred at 50° C. for 7 h. After cooling, aqueous NH$_4$Cl solution was added and the mixture was extracted with EtOAc (×3). The organic extracts were washed three times with water to remove DMF and then worked up as usual. The yellow solid produced was purified by flash chromatography on silica gel using 3% MeOH/CH$_2$Cl$_2$ as the eluant to afford alcohol 16 as a yellow solid (34 mg, 87%).

$^1$H NMR (500 MHz, CDCl$_3$): δ 3.80 (s, 3H), 3.81 (s, 3H), 4.61 (d, J=5.5 Hz 2H), 485 (d, J=5.4 Hz, 2H), 5.35 (m, 1H), 6.76 (d, J=5.5 Hz, 1H), 6.88-6.92 (m, 4H), 7.03 (d, J=6.8 Hz, 1H), 7.06 (d, J=5.7 Hz, 1H), 7.32 (d, J=8.4 Hz, 2H), 7.40 (d, J=8.4 Hz, 2H), 7.68 (d, J=6.8 Hz, 1H), 8.05 (d, J=5.5 Hz, 1H, 8.29 (d, J=5.7 Hz, 1H), 10.94 (m, 1H), 15.75 (br s, 1H); $^{13}$C NMR (75 MHz, CDCl$_3$): a 44.3, 452, 55.3 (2×CH$_3$), 100.3, 100.5, 106.9, 107.5, 111.4, 114.1 (2×C), 128.8, 129.2, 130.2 (2×C), 137.5, 142.8, 143.8, 145.4, 149.7, 158.6, 158.9, 159.0, 159.5, 159.8, 160.0; HRMS: Calcd for C$_{30}$H$_{27}$N$_7$O$_3$ (M$^+$) 533.2175, found 533.2185.

Example 4

Compound 19

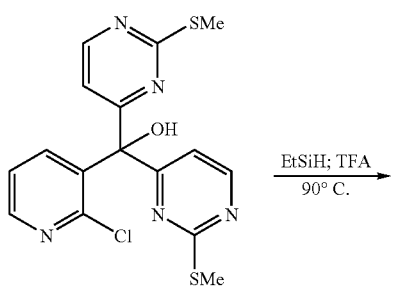

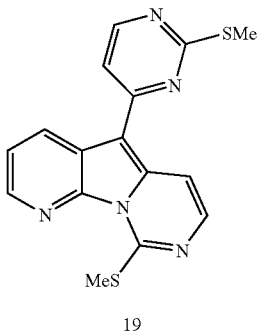

A mixture of alcohol 18 (prepared as described in Example 17 below) (1.04 g, 2.65 mmol), triethylsilane (3.4 ml, 21.5 mmol) and trifluoroacetic acid (0.81 ml, 10.6 mmol) was refluxed for 3 h. After cooling, the red residue was dissolved in CH$_2$Cl$_2$ (40 ml) and a saturated solution of NaHCO$_3$ was added. The brown mixture was stirred for 1 h at room temperature and the layers were separated. The aqueous layer was extracted with CH$_2$Cl$_2$ (3×50 ml) and the combined organic layers were dried, filtered and concentrated under reduced pressure. The red residue was purified by flash chromatography using ethyl acetate:hexane 1:4 to ethyl acetate:hexane 1:3 as eluent to afford the pyridopyrrolopyrimidine 19 (0.3 g, 33%) as a pale yellow solid. $^1$H NMR (300 MHz, CDCl$_3$): 8.64 (dd, J=8.1 and 1.7 Hz, 1H), 8.60 (dd, J=4.6 and 1.7 Hz, 1H), 8.51 (d, J=5.4 Hz, 1H), 8.06 (d, J=6.4 Hz, 1H), 7.82 (d, J=6.6 Hz, 1H), 7.51 (dd, J=8.5 and 4.6 Hz, 1H), 7.34 (d, J=5.4 Hz, 1H), 2.73 (s, 3H), 2.68 (s, 3H).

Example 5

Compounds 20 and 29

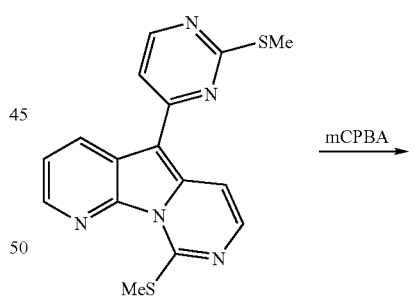

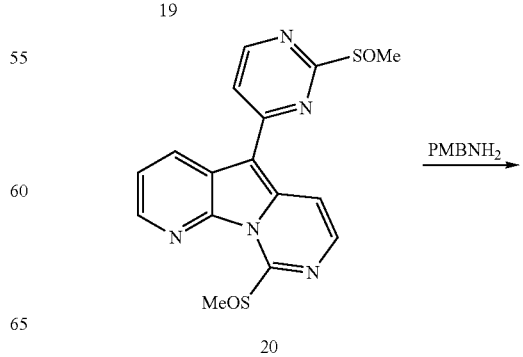

-continued

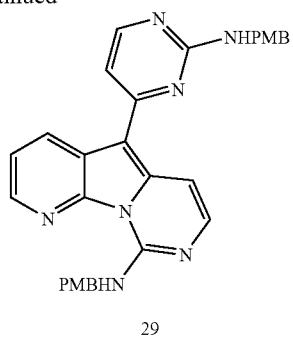

29

Oxidation of bis-sulfide 19 to bis-sulfoxide 20 was carried out by the same procedure described above in Example 2.

A mixture of p-methoxybenzylamine (2 ml) and bis-sulfinyldeoxyvariolin 20 (30 mg, 8.1×10⁵ mol) was stirred at 95° C. for 2 h and evaporated at reduced pressure. The red residue was purified by flash chromatography using DCM/MeOH (0.2%) to DCM/MeOH (2%) as eluent to afford N',N-bis(p-methoxybenzyl)deoxyvariolin 29 (21 mg, 49%) as a yellow oil. $^1$H NMR (300 MHz, CDCl$_3$): 10.4 (brs, 1H), 8.56 (d, J=7.8 Hz, 1H), 8.31 (d, J=5.4 Hz, 1H), 8.27 (dd, J=5.2 and 1.1 Hz, 1H), 7.63 (d, J=6.8 Hz, 1H), 7.42-7.33 (m, 12H), 6.98 (d, J=5.4 Hz, 1H), 6.93-6.89 (m, 4H), 5.52 (brs, 1H), 4.89 (d, J=5.4 Hz, 2H), 4.69 (d, J=5.9 Hz, 2H), 3.81 (s, 3H), 3.80 (s, 3H).

Example 6

Compound 28a

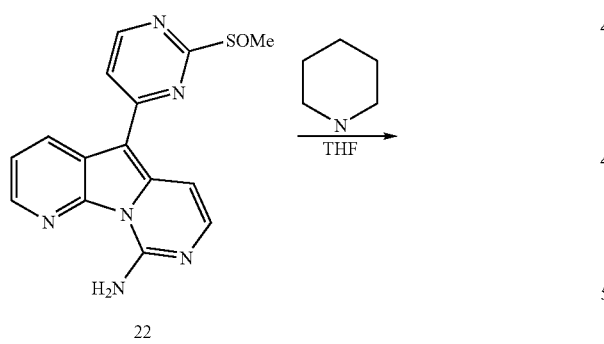

Piperidine (0.04 ml, 0.4 mmol) was added to a solution of sulfinyldeoxyvariolin 22 (7 mg, 2.1×10⁻⁵ mol) (prepared ae described in Process Example 5 below) in THF (2 ml).

The yellow solution was stirred at 70° C. overnight and evaporated at reduced pressure.

The yellow residue was purified by flash chromatography using DCM/MeOH (2%) to DCM/MeOH (3%) as eluent to afford piperidinyldeoxyvariolin 28a (5.6 mg, 78%) as a yellow oil. $^1$H NMR (300 MHz, CDCl$_3$): 8.63 (dd, J=8.4 and 1.5 Hz, 1H), 8.38 (dd, J=4.8 and 1.7 Hz, 1H), 8.35 (d, J=5.4, 1H), 7.60 (d, J=6.6 Hz, 1H), 7.50 (d, J=6.6 Hz, 1H), 7.46 (dd, J=8.0 and 4.6 Hz, 1H), 6.84 (d, J=5.4 Hz, 1H), 3.92 (brs, 4H), 1.73 (brs, 6H). MS (electrospray ionisation, ESI) 346 (M+1).

Example 7

Compound 28b

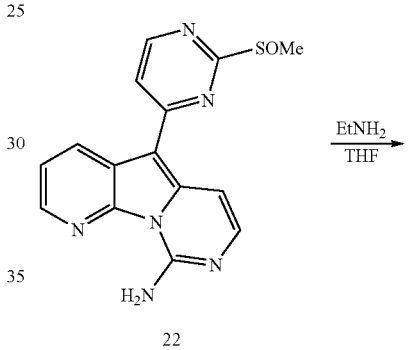

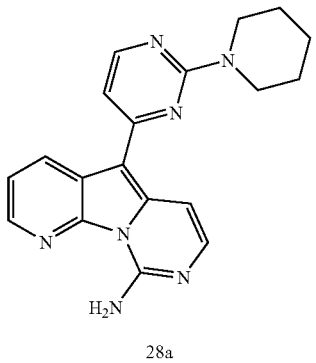

Ethylamine (0.34 ml, 2M in MeOH) was added to a solution of sulfinyldeoxyvariolin 22 (prepared as described in Process Example 5 below) (11 mg, 3.4×10⁻⁵ mol) in THF (2 ml). The yellow solution was stirred at 70° C. overnight and evaporated at reduced pressure. The yellow residue was purified by flash chromatography using DCM/MeOH (2%) to DCM/MeOH (4%) as eluent to afford N'-ethyldeoxyvariolin 28b (5.5 mg, 53%) as a yellow oil. $^1$H NMR (300 MHz, CDCl$_3$): 8.67 (dd, J=7.9 and 1.4 Hz, 1H), 8.36 (d, J=4.4, 1H), 8.22 (d, J=4.8, 1H), 7.52 (brs, 2H), 7.45 (dd, J=7.8 and 4.1 Hz, 1H), 6.93 (d, J=5.1 Hz, 1H), 3.54 (d, J=6.8 Hz, 2H), 1.29 (t, J=7.0, 3H). (ESI) 306 (M+1).

Example 8

Compound 28c

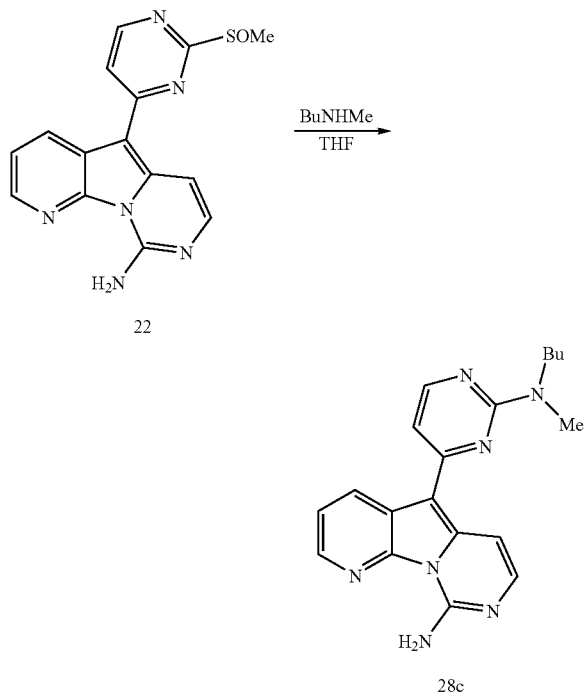

Butylmethylamine (0.029 ml, 0.24 mmol) was added to a solution of sulfinyldeoxyvarolin 22 (prepared as described in Process Example 5 below) (8 mg, $2.4 \times 10^{-5}$ mol) in THF (2 ml). The yellow solution was stirred at 70° C. overnight and evaporated at reduced pressure. The yellow residue was purified by flash chromatography using DCM/MeOH (2%) to DCM/MeOH (4%) as eluent to afford N'-butylmethyldeoxyvariolin 28c (2 mg, 62% based on recovered starting material) as a yellow oil. $^1$H NMR (300 MHz, CDCl$_3$): 8.75 (d, 1H), 8.41 (dd, 1H), 8.39 (d, J=5.5, 1H), 7.78 (d, J=6.5 Hz, 1H), 7.68 (d, J=6.5 Hz, 1H), 7.42 (dd, J=8.0 and 4.5 Hz, 1H), 6.89 (d, J=5.6 Hz, 1H), 3.60 (brs, 2H), 3.41 (s, 3H), 1.62 (brs, 4H), 1.05 (brs, 3H). (EST) 348 (M+1).

Example 9

Compound 28d

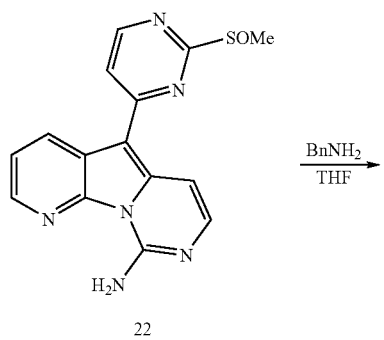

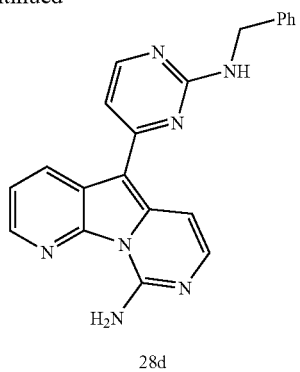

Benzylamine (0.050 ml, 0.45 mmol) was added to a solution of sulfinyldeoxyvariolin 22 (4 mg, $1.2 \times 10^5$ mol) in THF (1.5 ml). The yellow solution was stirred at 70° C. overnight and evaporated at reduced pressure. The yellow residue was purified by flash chromatography using DCM/MeOH (2%) to DCM/MeOH (4%) as eluent to afford N'-benzyldeoxyvariolin 28d (2.1 mg, 47%) as a yellow oil. $^1$H NMR (300 MHz, CDCl$_3$): 8.81 (brs, 1H), 8.75 (d, J=7.1, 1H), 8.64 (d, J=6.0 Hz, 1H), 7.49-7.31 (m, 8H), 6.99 (d, J=6.2 Hz, 1H), 4.78 (d, J=5.8 Hz, 2H). (ESI) 368 (M+1).

Example 10

Compound 27

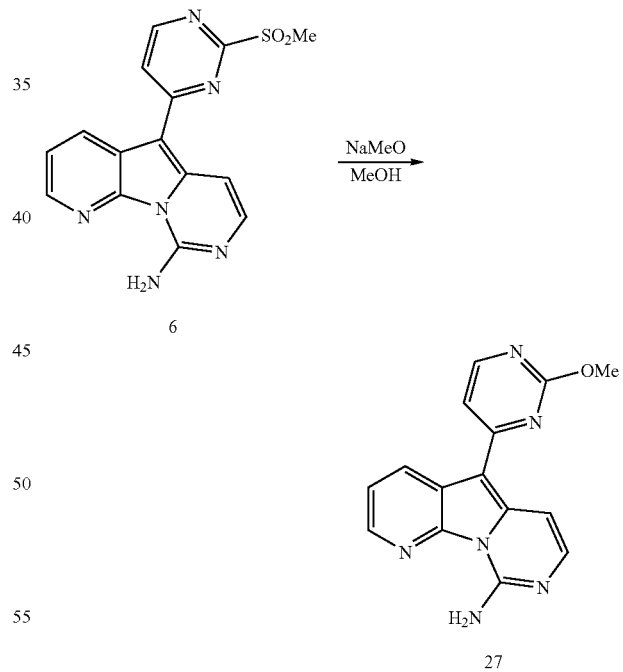

A solution of sulfonyldeoxyvariolin 6 (prepared as described in Process Example 5 below) (5.8 mg, $1.7 \times 10^{-5}$ mol) in MeOH (2 ml) was added to a solution of sodium methoxide in MeOH (2 ml) at 0° C. The yellow solution was stirred at 24° C. for 4 h, quenched with a saturated solution of NH$_4$Cl and extracted with ethyl acetate (3×10 ml). The combined organic layers were dried, filtered and evaporated under reduced pressure. The yellow residue was purified by flash chromatography using DCM/MeOH (1%) to DCM/MeOH (3%) as eluent to afford methoxydeoxyvariolin 27

(2.6 mg, 53%) as a yellow solid $^1$H NMR (300 MHz, CDCl$_3$): 8.78 (dd, J=8.1 and 1.5 Hz, 1H), 8.51 (d, J=5.43 Hz, 1H), 8.41 (dd, J=4.6 and 1.5 Hz, 1H), 7.69 (d, J=6.6 Hz, 1H), 7.63 (d, J=6.6 Hz, 1H), 7.50 (dd, J=8.1 and 4.6 Hz, 1H), 7.34 (d, J=5.4 Hz, 1H), 4.14 (s, 3H). (ESI) 293 (M+1).

Example 11

Compound 26

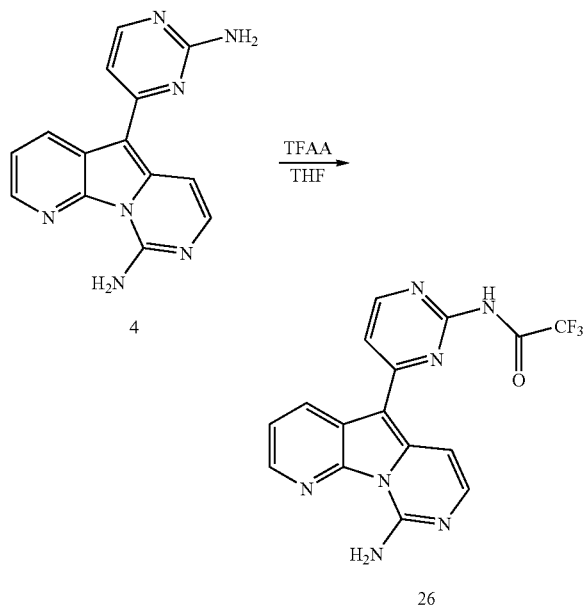

Trifluoroacetic anhydride (6 nil, 4.3×10$^5$ mol) was added to a solution of deoxyvariolin 4 (4 mg, 1.4×10$^{15}$ mol) in THF (1.5 ml). The yellow solution was stirred at 24° C. overnight and evaporated at reduced pressure. The yellow residue was dissolved in DCM (5 ml) and washed with a saturated solution of NaHCO$_3$ (4 ml). The organic layer was dried, filtered and evaporated under reduced pressure. The yellow residue was purified by flash chromatography using DCM/MeOH (2%) to DCM/MeOH (4%) as eluant to afford N'-trifluoroacetyldeoxyvariolin 26 (0.9 mg, 43% based on recovered starting material) as a yellow oil. $^1$H NMR (300 MHz, CDCl$_3$): 8.99 (dd, J=8.4 and 1.1 Hz, 1H), 8.57 (d, J=5.6 Hz, 1H), 8.42 (dd, J=4.6 and 1.3 Hz, 1H), 7.91 (d, J=6.7 Hz, 1H), 7.79 (d, J=6.6 Hz, 1H), 7.58 (dd, J=8.3 and 4.3 Hz, 1H), 7.52 (d, J=5.6 Hz, 1H). (ESI) 374 (M+1).

Example 12

Compound 25

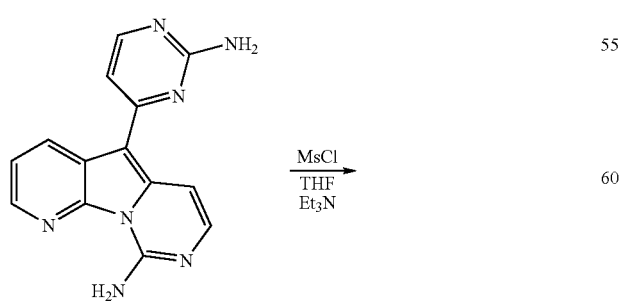

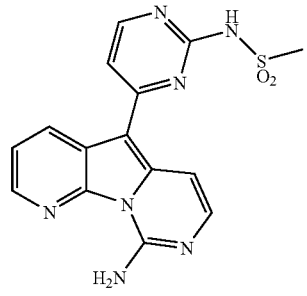

Methanesulfonyl chloride (5.5 µl, 5×10$^{-5}$ mol) was added to a solution of deoxyvariolin 4 (prepared as described in Process Example 2 or 4 below) (5 mg, 1.8×10$^{-5}$ mol) and Et$_3$N (5 µl, 3.6×10$^{-5}$ mol) in THF (1.5 ml). The yellow solution was stirred at 240° C. overnight and evaporated at reduced pressure. The yellow residue was dissolved in DCM (5 ml) and washed with a saturated solution of NaHCO$_3$ (4 ml). The organic layer was dried, filtered and evaporated under reduced pressure. The yellow residue was purified by flash chromatography using DCM/MeOH (2%) to DCM/MeOH (4%) as eluant to afford N'-methanesulfonyldeoxyvariolin 25 (1.5 mg, 46% based on recovered starting material) as a yellow oil. $^1$H NMR (300 MHz, CDCl$_3$): 8.89 (dd, J=7.9 and 1.1 Hz, 1H), 8.76 (d, J=5.7 Hz, 1H), 8.42 (dd, J=42 and 1.2 Hz, 1H), 7.78 (d, J=6.4 Hz, 1H), 7.72 (d, J=6.5 Hz, 1H), 7.64 (d, J=5.6 Hz, 1H), 7.57 (dd, J 8.3 and 4.3 Hz, 1H), 3.15 (s, 3H).

Example 13

Compounds 24a and 24b

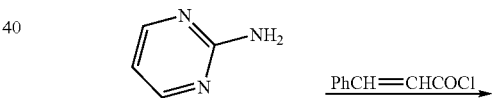

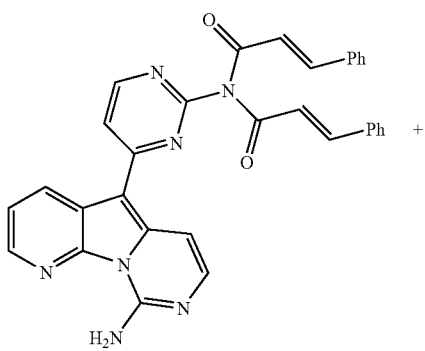

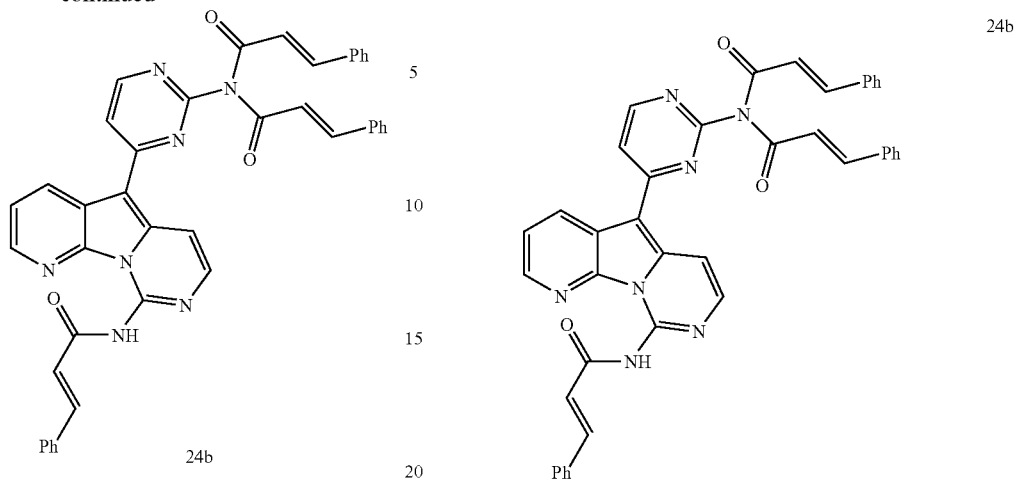

-continued

24b

Cinnamoyl chloride (9 μl, $5.4\times10^{-5}$ mol) was added to a solution of deoxyvariolin 4 (5 mg, $1.8\times10^{5}$ mol) (prepared as described in Process Example 2 or 4 below) and $Et_3N$ (12 μl, $5.4\times10^{-5}$ mol) in THF (2 ml). Immediately, DMAP (1 mg, $0.9\times10^{-5}$ mol) was added in one portion, the yellow solution was stirred at 24° C. overnight and evaporated at reduced pressure. The yellow residue was dissolved in DCM (5 ml) and washed with a saturated solution of $NaHCO_3$ (4 ml). The organic layer was dried, filtered and evaporated under reduced pressure. The yellow residue was purified by flash chromatography using DCM/MeOH (1%) to DCM/MeOH (4%) as eluent to afford N'-biscinnamoyldeoxyvariolin 24a (1.1 mg, 21% based on recovered starting material) and N'-biscinnamoyl-N-cinnamoyldeoxyvariolin 24b (0.6 mg, 9% based on recovered starting material) as yellow oils.

24a $^1H$ NMR (300 MHz, $CDCl_3$): 8.78 (d, J=6.4, 1H), 8.69 (dd, J=7.4 and 1.1 Hz, 1H), 8.38 (dd, J=4.6 and 1.2 Hz, 1H), 7.91 (d, J=15.3 Hz, 2H), 7.64-7.32 (m, 14H), 6.90 (d, J=15.6 Hz, 2H). (ESI) 560 (M+Na), 538 (M+1).

24b $^1H$ NMR (300 MHz, $CDCl_3$): $^1H$ NMR (300 MHz, $CDCl_3$): 8.82 (d, J=6.4, 1H), 8.79 (dd, J=7.4 and 1.1 Hz, 1H), 8.58 (dd, J=4.6 and 1.3 Hz, 1H), 8.01-7.82 (m, 4H), 7.71 (d, J=15.3 Hz, 2H), 7.64 (dd, J=8.3 and 4.2 Hz, 1H), 7.58-7.31 (m, 16H), 6.90 (d, J=15.6 Hz, 3H). (ESI) 668 (4+1), 690 (M+Na).

Example 14

Compounds 23a, 23b and 23c

4

23a

-continued

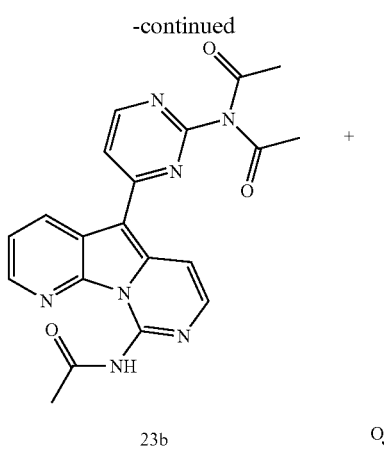

23b

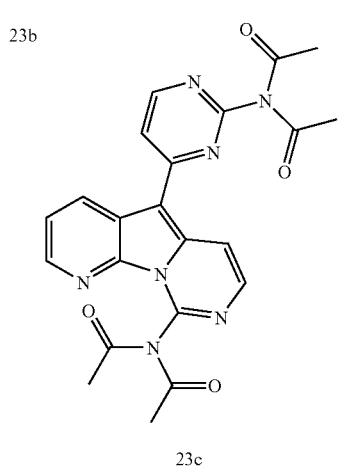

23c

Acetyl chloride (3.5 μl, 4.8×10⁻⁵ mol) was added to a solution of deoxyvariolin 4 (9 mg, 3.2×10⁻⁵ mol) (prepared as described in Process Example 2 or 4 below) and Et₃N (9 μl, 6.5×10⁻⁵ mol) in THF (2 ml). The orange slurry was stirred at 24° C. overnight and evaporated at reduced pressure. The yellow residue was dissolved in DCM (5 ml) and washed with a saturated solution of NaHCO₃ (4 ml). The organic layer was dried, filtered and evaporated under reduced pressure. The yellow residue was purified by flash chromatography using DCM/MeOH (2%) to DCM/MeOH (5%) as eluent to afford N'-bisacetyldeoxyvariolin 23a (1 mg, 26% based on recovered starting material), N'-bisacetyl-N-acetyldeoxyvariolin 23b (1 mg, 23% based on recovered starting material) and N'-bisacetyl-N-bisacetyldeoxyvariolin 23c (0.5 mg, 10% based on recovered starting material) as yellow oils.

23a $^1$H NMR (300 MHz, CDCl$_3$): 8.76 (d, J=5.6, 1H), 8.68 (dd, J=6.9 and 1.1 Hz, 1H), 8.42 (dd, J=4.1 and 1.2 Hz, 1H), 7.73 (d, J=6.6 Hz, 1H), 7.66 (d, J=6.6 Hz, 1H), 7.54-7.42 (m, 2H), 2.41 (s, 6H). (ESI) 384 (M+Na).

23b

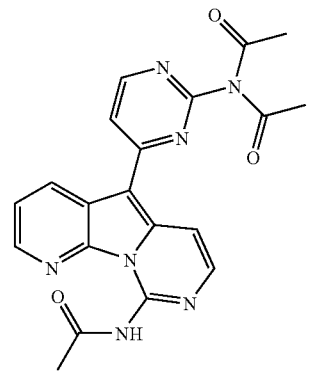

$^1$H NMR (300 MHz, CDCl$_3$): 8.82 (d, J=5.6 Hz, 1H), 8.72 (dd, J 7.8 and 1.2 Hz, 1H), 8.53 (dd, J=4.4 and 1.2 Hz, 1H), 7.90 (d, J=6.4 Hz, 1H), 7.87 (d, J=6.5 Hz, 1H), 7.70 (d, J=5.4 Hz, 1H), 7.60 (dd, J=8.3 and 4.9 Hz, 1H), 2.68 (s, 3H), 2.40 (s, 6H). (ESI) 426 (M+Na), 404 (M+1).

23c $^1$H NMR (300 MHz, CDCl$_3$): 8.88 (d, J=5.4 Hz, 1H), 8.63 (dd, J=8.3 and 1.7 Hz, 1H), 8.56 (dd, J=4.6 and 1.3 Hz, 1H), 8.36 (d, J=6.7 Hz, 1H), 7.99 (d, J=6.6 Hz, 1H), 7.75 (d, J=5.5 Hz, 1H), 7.58 (dd, J=8.3 and 4.6 Hz, 1H), 2.43 (s, 12H). (ESI) 468 (M+Na).

Example 15

Compounds 23d and 23e

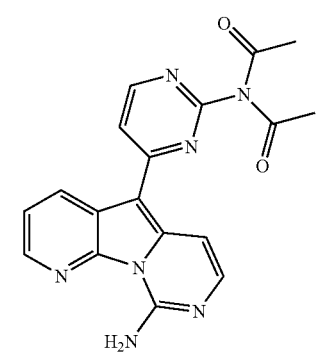 

4

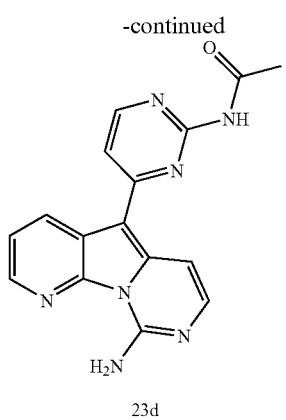

23d

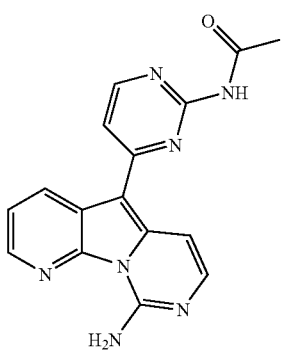

23e

Acetyl chloride (1.5 μl, 1.8×10⁻⁵ mol) was added to a solution of deoxyvariolin 4 (prepared as described in Process Example 2 or 4 below) (5 mg, 1.8×10⁻⁵ mol) and Et₃N (4 μl, 2.7×10⁻⁵ mol) in THF (1.5 ml) at −78° C. The orange slurry was stirred overnight increasing the temperature very slowly until room temperature and afterwards evaporated at reduced pressure. The yellow residue was dissolved in DCM (5 ml) and washed with a saturated solution of NaHCO₃ (4 ml). The organic layer was dried, filtered and evaporated under reduced pressure. The yellow residue was purified by flash chromatography using DCM/MeOH (1%) to DCM/MeOH (4%) as eluent to afford N'-acetyl-N-acetyldeoxyvariolin 23d (1 mg, 26%) and N'-acetyldeoxyvariolin 23e (0.5 mg, 10%) as yellow oils.

23d

¹H NMR (300 MHz, CDCl₃): 8.83 (dd, J=7.4 and 1.4 Hz, 1H), 8.52 (d, J=6.2, 1H), 8.41 (dd, J=4.2 and 1.4 Hz, 1H), 7.75-7.71 (m, 2H), 7.56-7.48 (m, 1H), 7.39 (d, J=6.3 Hz, 1H), 2.43 (s, 3H). (ESI) 342 (M+Na).

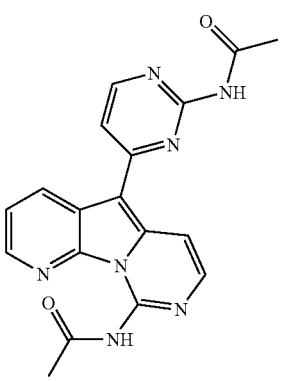

23e

¹H NMR (300 MHz, CDCl₃): 8.91 (dd, J=7.4 and 1.4 Hz, 1H), 8.58 (d, J=6.2, 1H), 8.52 (dd, J=4.2 and 1.4 Hz, 1H), 8.19 (d, J=6.4 Hz, 1H), 8.03 (brs, 1H), 7.85 (d, J=6.5 Hz, 1H), 7.61 (dd, J=8.3 and 4.9 Hz, 1H), 7.39 (d, J=6.1 Hz, 1H), 2.65 (s, 3H), 2.43 (s, 3H). (EST) 384 (M+Na).

Example 16

Compound 12

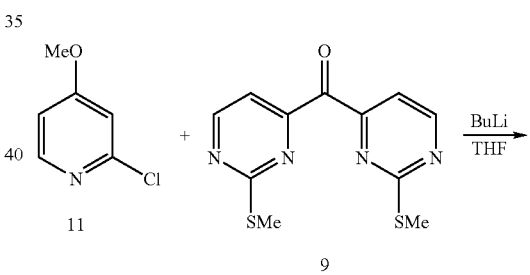

12

2-Chloro-4-methoxypyridine (11) (Reference Example 3) (0.633 g, 4.41 mmol) was dissolved in freshly distilled THF (18 mL) and the reaction cooled to below −90° C. n-BuLi in hexanes (1.6 M, 2.9 mL, 4.5 mmol) was added over a period of 17 min to the stirred solution, keeping the temperature below −97° C. The orange solution was then stirred at −78° C. for 1 h, by which time it had become a wine-red colour. The reaction mixture was re-cooled to below −90° C. and a solution of ketone (9) (1.14 g, 4.09 mmol) in THF (10 mL)

was added over 11 min, keeping the temperature below −90° C. The dark mixture was stirred at −78° C. for 3.5 h, then quenched with methanol and allowed to warm to room temperature. The reaction mixture was shaken with aqueous NH₄Cl solution, extracted with ethyl acetate (×3) and subjected to standard workup. The crude mixture was purified by flash chromatography on silica gel using gradient elution (70 to 75% EtOAc/hexanes) to give the triaryl alcohol 12 as a cream solid (1.32 g, 76%).

¹H NMR (500 MHz, CDCl₃): δ 2.49 (s, 6H), 3.43 (s, 3H), 6.55 (s, 1H), 6.76 Hz, 1H), 7.39 (d, J=5.4 Hz, 2H), 8.25 (d, J=5.4 Hz, 1H), 8.46 (d, J=5.4 Hz, 2H); ¹³C NMR (75 ME CDCl₃): δ 14.1, 55.8, 78.0, 107.1, 113.7, 124.8, 149.8, 152.3, 157.2, 165.9, 171.0, 171.1; IR (CDCl₃ solution): 3344 cm⁻¹; HRMS: Calcd for $C_{17}H_{16}{}^{35}ClN_5O_2{}^{32}S_2$ (M⁺) 421.0434, found 421.0448.

Example 17

Compound 18

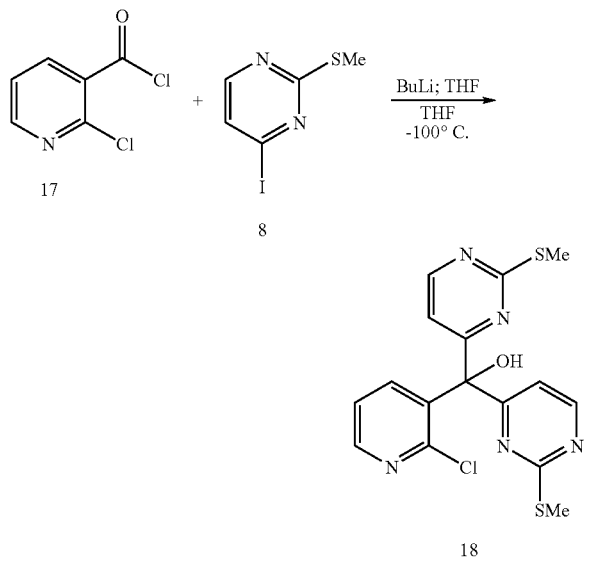

BuLi (6.9 ml, 2.5 M in hexane) was added dropwise to a solution of iodopyrimidine 8 (Reference Example 1) (4.3 g, 17 mmol) in THF (50 ml) at −100° C. The black solution was stirred for 30 min at the same temperature. A solution of 2-chloronicotinoyl chloride 17 (1 g, 5.7 mmol) in THF (7 ml), previously cooled at −78° C., was added via cannula. The intense red mixture was stirred for 3 h at −95° C. and a saturated solution of NH₄Cl (50 ml) was added. The layers were separated and the aqueous layer was extracted with diethyl ether (3×100 ml). The combined organic layers were dried, filtered and concentrated under reduced pressure. The red residue was purified by flash chromatography using ethyl acetate:hexane 1:3.5 to ethyl acetate:hexane 1:1.5 as eluent to afford the alcohol 18 (1.3 g, 58%) as a pale orange solid. ¹H NMR (300 MHz, CDCl₃): 8.56 (d, J=5.1H. 2H), 8.37 (dd, J 4.7 and 1.5, 1H), 7.39 (d, J=5.1 Hz, 2H), 7.22 (dd, J=7.8 and 1.9, 1H), 7.17 (dd, J=7.8 and 4.4 Hz, 1H), 2.48 (s, 6H).

Process Example 1

Compound 1 (Variolin)

(This compound is not part of the present invention)

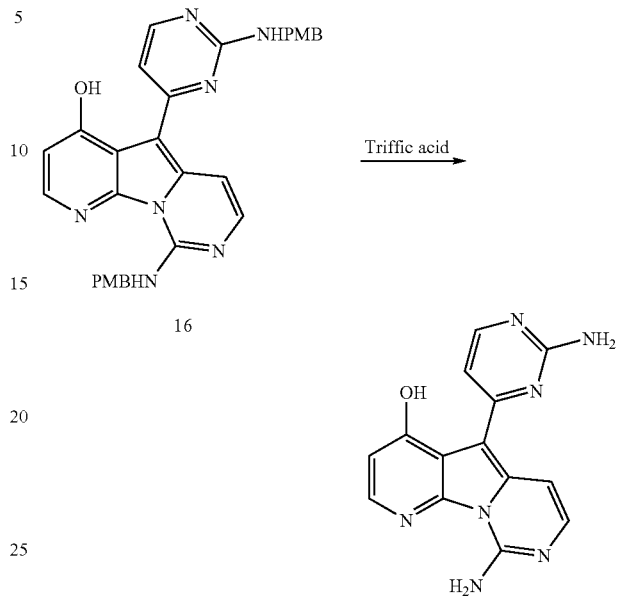

Alcohol 16 (prepared as described in Example 3 above) (33 mg, 0.062 mmol) was dissolved in neat triflic acid (0.4 mL) under atmospheric conditions. The flask was sealed and the deep red solution was left at room temperature for 5 h. The flask was cooled in ice and MeOH (2 mL) was added dropwise. Addition of concentrated aqueous ammonia (2 mL) produced a bright yellow precipitate. The suspension was applied to the top of a chromatography column containing reverse-phase silica, which had been equilibrated with 50% MeOH/water. The yellow suspension was applied to the column with 20% MeOH/water (50 mL). The polarity of the eluting solvent system was decreased to 80% MeOH/water (50 mL), and then to 85% MeOH/water containing 0.1% TFA, whereupon the yellow product began to elute. The bright yellow fractions were combined and concentrated in vacuo to give variolin B as its trifluoroacetate salt MeOH (10 mL) was added, followed by concentrated aqueous ammonia (1-2 mL) to give the free base. Removal of the solvents under reduced pressure, followed by drying (35° C., 0.03 mm Hg) overnight gave variolin B (1) (10 mg, 55%), which was identical in all aspects with the natural material.

Process Example 2

Compound 4 (Deoxyvariolin)

(This compound is not part of the present invention)

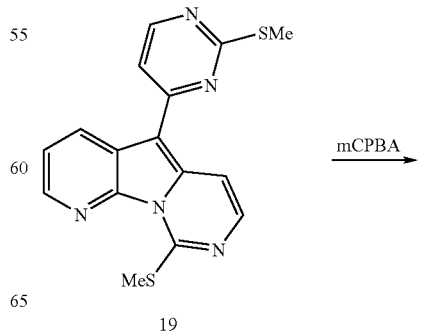

-continued

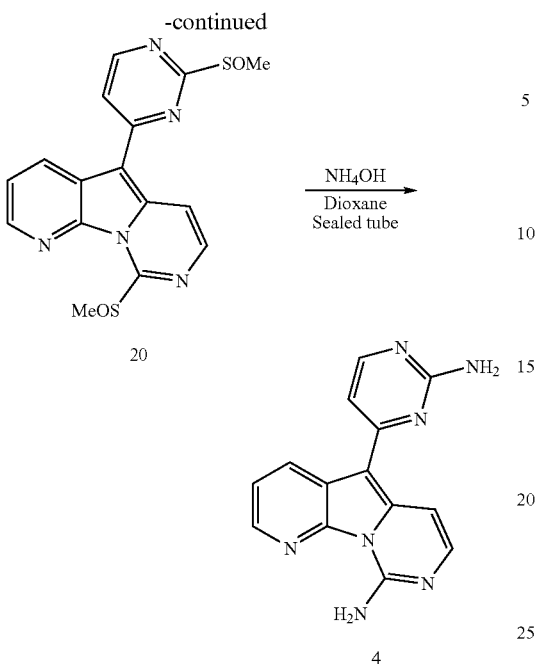

A solution of mCPBA (Aldrich 70%) (98 mg, 0.39 mmol) in DCM (4 ml), previously dried over Na$_2$SO$_4$, was added dropwise to a cooled (−30° C.) solution of dithioether 19 (Example 4) (61 mg, 0.18 mmol) in DCM (5 ml). The yellow solution was stirred for 15 min at 0° C. A saturated aqueous Na$_2$S$_2$O$_3$ solution (5 ml) was added and the organic layer was washed with a saturated solution of NaHCO$_3$ (5 ml). The combined aqueous layers were extracted with DCM (3×10 ml). The combined organic extracts were dried, filtered and concentrated. The yellow residue was poured in a sealed tube with dioxane (4 ml) and ammonia solution 32% (8 ml) was added. The brown mixture was stirred for 14 h at 85° C. The resulting yellow mixture was evaporated in vacuo and DCM/MeOH (10:1) (11 ml) were added, the solution dried and the solvent evaporated at reduced pressure. The yellow solid was purified by flash chromatography using DCM/MeOH (2%) to DCM/MeOH (5%) as eluent to afford deoxyvariolin 4 (14 mg, 29%, 2 steps) as a yellow solid. $^1$H NMR (300 MHz, DMSO): 8.92 (dd, J=8.1 and 1.5 Hz, 1H), 8.45 (dd, J=4.6 and 1.4 Hz, 1H), 8.22 (d, J=5.5, 1H), 7.68 (d, J=6.6 Hz, 1H), 7.63 (d, J=6.6 Hz, 1H), 7.58 (dd, J=8.1 and 4.6 Hz, 1H), 7.06 (d, J=5.4 Hz, 1H). (ESI) 278 (M+1).

Process Example 3

Compound 5 (Thiodeoxyvariolin)

(This compound is not part of the present invention)

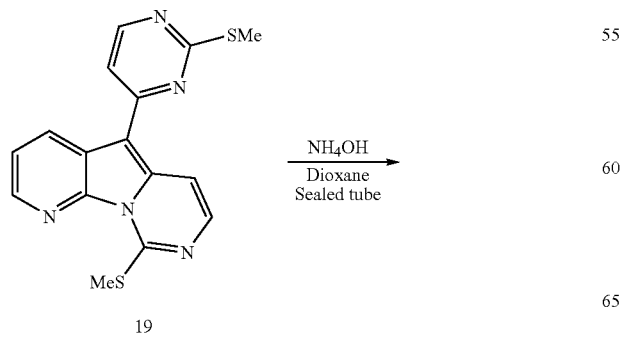

-continued

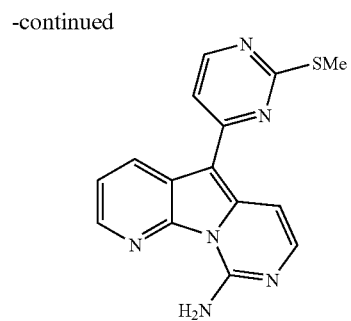

Ammonia solution 32% (3 ml) was added to a solution of dithioether 19 (Example 4) (12 mg, 0.035 mmol) in dioxane (2 ml). The brown mixture was stirred for 14 h at 85° C. in a sealed tube. The resulting yellow mixture was evaporated in vacuo, DCM (5 ml) was added, the solution dried and the solvent evaporated at reduced pressure. The yellow solid was purified by flash chromatography using DCM/MeOH (2%) to DCM/MeOH (3%) as eluent to afford thiodeoxy-variolin 5 (8 mg, 73%) as a yellow solid. $^1$H NMR (300 MHz CDCl$_3$): 8.72 (dd, J=8.1 and 1.5 Hz, 1H), 8.48 (d, J=5.4 Hz, 1H), 8.39 (dd, J=4.8 and 1.6 Hz, 1H), 7.66 (d, J=6.8 Hz, 1H), 7.56 (d, J=6.7 Hz, 1H), 7.48 (dd, J=8.1 and 4.6 Hz, 1H), 7.32 (d, J=5.3 Hz, 1H), 2.67 (s, 3H). (ESI) 309 (M+1).

Process Example 4

Compound 4 (Deoxyvariolin)

(This compound is not part of the present invention)

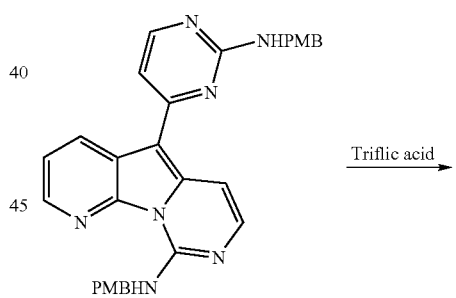

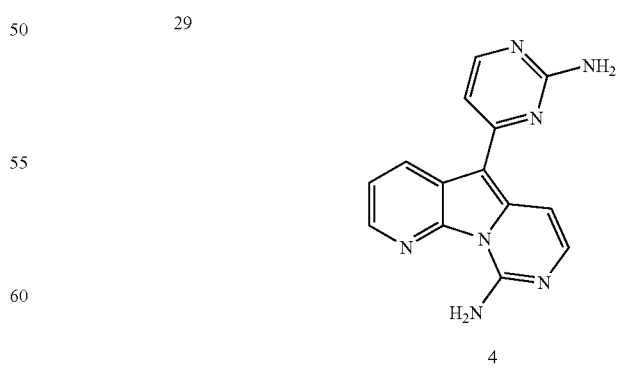

N',N-bis (p-methoxybenzyl)deoxyvariolin 29 (Example 5) (15 mg, 2.9×10$^{-5}$ mol) was treated with neat triflic acid (1.5 ml) and stirred for 17 h at 24° C. The black solution was evaporated at reduced pressure and the black slurry was dissolved in DCM (4 ml) and washed with a saturated solution of NaHCO$_3$ (5 ml). The aqueous layer was extracted with DCM (3×5 ml) and the combined organic layers were dried, filtered and evaporated. The brown residue was purified by flash chromatography using DCM/MeOH (1%) to DCM/MeOH (5%) as eluent to afford deoxyvariolin 4 (1.5 mg, 19%) as a yellow solid. $^1$H NMR (300 MHz, DMSO): 8.92 (dd, J 8.1 and 1.5 Hz, 1H), 8.45 (dd, J=4.6 and 1.4 Hz, 1H), 8.22 (d, J=5.5, 1H), 7.68 (d, J=6.6 Hz, 1H), 7.63 (d, J=6.6 Hz, 1H), 7.58 (dd, J=8.1 and 4.6 Hz, 1H), 7.06 (d, J=5.4 Hz, 1H). (ESI) 278 (M+1).

Process Example 5

Compounds 6 and 22

(These compounds are not part of the present invention)

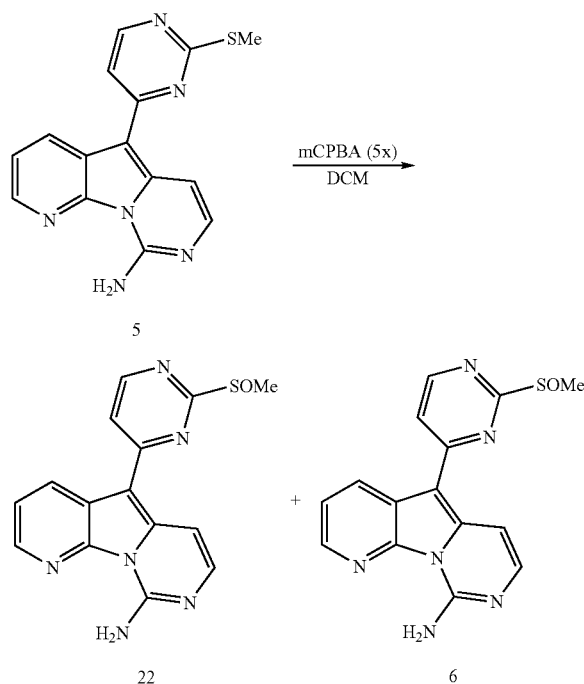

A solution of mCPBA (Aldrich 70%) (70 mg, 0.30 mmol) in DCM (3 ml), previously dried over Na$_2$SO$_4$, was added dropwise to a solution of thiodeoxyvariolin 5 (39 mg, 0.13 mmol) in DCM (7 ml). The yellow solution was stirred for 2 h at 24° C. A saturated aqueous Na$_2$S$_2$O$_3$ solution (5 ml) was added and the organic layer was washed with a saturated solution of NaHCO$_3$ (5 ml). The combined aqueous layers were extracted with DCM (3×20 ml). The combined organic extracts were dried, filtered and concentrated. The yellow residue was purified by flash chromatography using DCM/MeOH (2%) to DCM/MeOH (5%) as eluent to afford sulfinyldeoxyvariolin 22 (15 mg, 35%) as a yellow oil and sulfonyldeoxyvariolin 6 (25 mg, 58%) as a yellow solid.

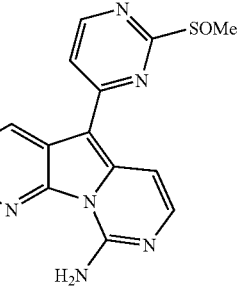

$^1$H NMR (300 MHz, CDCl$_3$): 8.86 (dd, J=8.1 and 1.5 Hz, 1H), 8.74 (d, J=5.6 Hz, 1H), 8.43 (dd, J=4.6 and 1.3 Hz, 1H), 7.77 (d, J=6.8 Hz, 1H), 7.72 (d, J=6.6 Hz, 1H), 7.67 (d, J=5.8 Hz, 1H), 7.54 (dd, J=8.0 and 4.6 Hz, 1H), 3.02 (s, 3H). (ESI) 325 (M+1).

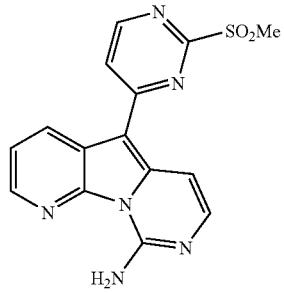

$^1$H NMR (300 MHz, CDCl$_3$): 8.80 (dd, J=8.1 and 1.4 Hz, 1H), 8.71 (d, J=5.6 Hz, 1H), 8.41 (dd, J=4.8 and 1.4 Hz, 1H), 7.76 (d, J=5.6 Hz, 1H), 7.74 (d, J=6.4 Hz, 1H), 7.64 (d, J=6.4 Hz, 1H), 7.52 (dd, J=8.2 and 4.8 Hz, 1H), 3.40 (s, 3H).

Reference Example 1

Compound 8

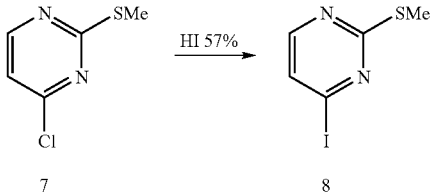

Iodopyrimidine 8 was prepared following the experimental procedure described in the literature: Majeed, A. J.; Antonsen. O.; Benneche, T.; Undheim, K. Tetrahedron 1989, 45, 993.

Reference Example 2

Compound 9

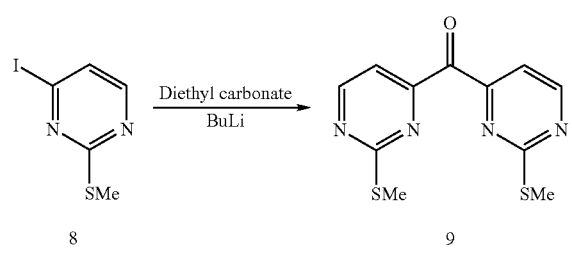

A pre-cooled (−97° C.) solution of n-BuLi in hexanes (1.55 M, 10.0 mL, 15.5 mmol) was added slowly over a period of 21 min to a solution of 4-iodo-2-methylthiopyrimidine (8) (3.90 g, 15.5 mmol) in freshly distilled THF (47 mL) at −97° C. (methanol/liquid $N_2$ bath). Care was taken to prevent the temperature from rising above −97° C. After addition was complete, the dark mixture was stirred for 30 min at −97° C. and then, a pre-cooled (−97° C.) solution of diethyl carbonate (0.94 mL, 7.8 mmol) in THF (4 mL) was added over a period of approx. 3 min. After 15 min at −97° C. the bath was allowed to warm to −35° C. over 2 h, and then to room temperature. The reaction mixture was shaken with aqueous $NH_4Cl$ and extracted with EtOAc (×3). After the usual workup, the crude material was partially purified by vacuum distillation in a Kügelrohr apparatus (160° C., 0.03 mm Hg). Further purification was achieved by flash chromatography on silica gel using gradient elution (25, 30 and then 50% EtOAc/hexanes) to afford pure ketone 9 as a yellow solid (1.14 g, 53%).

Mp: 106-107° C.; $^1$H NMR (500 MHz, $CDCl_3$): δ 2.51 (s, 6H), 7.54 (d, J=4.9 Hz, 2H), 8.79 (d, J=4.9 Hz, 2H); $^{13}$C NMR (75 MHz, $CDCl_3$): δ 14.2, 114.9, 158.8, 159.2, 173.2, 190.7; IR (KBr disc): 1695 cm$^{-1}$; HRMS: Calcd for $C_{11}H_{10}N_4O^{32}S_2$ ($M_+$) 278.0296, found 278.0289.

Reference Example 3

Compound 11

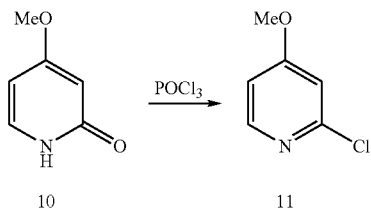

4-Methoxy-2-pyridone (10) (0.805 g, 6.43 mmol) and freshly distilled $POCl_3$ (8 mL) were heated at reflux for 15 h. Excess $POCl_3$ was removed in vacuo and the resultant viscous oil was cooled in ice and carefully neutralised with saturated $NaHCO_3$ solution. The mixture was extracted with EtOAc (×3) and the extracts were worked up in the standard manner to give a brown oil. This material was partially purified by vacuum distillation in a Kugelrohr apparatus (100° C., 0.07 mm Hg). The distillate was triturated with petroleum ether and a white precipitate was filtered off. The filtrate was concentrated and final purification by flash chromatography on silica gel using 30% EtOAc/hexanes as the eluant gave 2-chloro-4-methoxypyridine (11) as a colourless oil (0.586 g, 63%).

The invention claimed is:
1. A compound of formula (I):

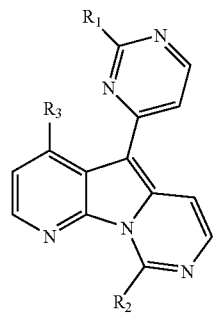

(I)

wherein:
$R_1$ and $R_2$ are each independently selected from the group consisting of H, OH, OR', SH, SR', SOR', $SO_2R'$, $NO_2$, $NH_2$, NHR', N(R')$_2$, NHCOR', N(COR')$_2$, $NHSO_2R'$, CN, halogen, C(=O)H, C(=O)R', $CO_2H$, $CO_2R'$, $C_1$-$C_{12}$ alkyl, $C_1$-$C_{12}$ haloalkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic; and $R_3$ is selected from the group consisting of OH and OMe;

wherein each R' group is independently selected from the group consisting of OH, $C_1$-$C_{12}$ alkyl, $C_1$-$C_{12}$ haloalkyl, $C_2$-$C_{12}$ alkenyl, $C_2$-$C_{12}$ alkynyl, substituted or unsubstituted aryl, substituted or unsubstituted aralkyl, substituted or unsubstituted arylalkenyl and substituted or unsubstituted heteroaromatic, and wherein when the group $R_1$ or $R_2$ is a group of formula N(R')$_2$ or N(COR')$_2$, each of the R' groups may be the same or different, or the two R' groups, together with the nitrogen atom to which they are attached, may form a 5-14 membered heterocyclic ring;

the aryl group and the aryl moiety of the aralkyl and arylalkenyl group is a carbocyclic aryl group having from 6 to 14 carbon atoms in a carbocyclic ring or two or more fused rings;

the aralkyl group is a $C_1$-$C_6$ alkyl group which is substituted by an aryl group as defined above;

the arylalkenyl group is a $C_2$-$C_6$ alkenyl group which is substituted by an aryl group as defined above;

the heteroaromatic group is a heterocyclic aromatic group having from 5 to 14 ring atoms in one ring or two or more fused rings of which at least one ring atom is selected from the group consisting of nitrogen, oxygen and sulphur, and such a heterocyclic aromatic group fused with an aryl group as defined above;

the substituents on the aryl and heteroaromatic groups and the aryl moiety of the aralkyl and arylalkenyl groups are selected from the group consisting of $C_1$-$C_{12}$ alkyl, $C_1$-$C_{12}$ haloalkyl, $C_1$-$C_{12}$ alkoxy, $C_1$-$C_{12}$ alkylthio, $NH_2$, $C_1$-$C_6$ alkylamino, di($C_1$-$C_6$ alkyl)amino, $C_1$-$C_4$ alkanoylamino, di($C_1$-$C_4$ alkanoyl)amino, $NO_2$, CN and halogen;

and wherein one or more of the tertiary amine nitrogen atoms of formula (I) is optionally quaternised, or a pharmaceutically acceptable salt thereof,
with the exception of the compounds wherein:
$R_1$ and $R_2$ are amino and $R_3$ is hydroxy.

2. A compound according to claim 1, wherein $R_1$ is selected from the group consisting of OH, OR', SH, SR', SOR', $SO_2R'$, $NH_2$, NHR', N(R')$_2$, NHCOR', N(COR')$_2$, $NHSO_2R'$, C(=O)R', $CO_2H$, $CO_2R'$, $C_1$-$C_{12}$ alkyl and $C_1$-$C_{12}$ haloalkyl, each R' group being independently selected from the group consisting of OH, $C_1$-$C_{12}$ alkyl, $C_1$-$C_{12}$ haloalkyl, aryl (which may optionally be substituted with a group selected from $C_1$-$C_6$ alkyl, $C_1$-$C_6$ alkoxy, $C_1$-$C_6$ alkylthio, $NH_2$, $C_1$-$C_6$ alkylamino, di($C_1$-$C_6$ alkyl)amino, $NO_2$, CN and halogen), aralkyl or arylalkenyl (the aryl moiety of which may optionally be substituted with a group selected from $C_1$-$C_6$ alkyl, $C_1$-$C_6$ alkoxy, C1-$C_6$ alkylthio, $NH_2$, $C_1$-$C_6$ alkylamino, di($C_1$-$C_6$ alkyl)amino, $NO_2$, CN and halogen), and wherein when the group $R_1$ is a group of formula N(R')$_2$ or N(COR')$_2$, each of the R' groups may be the same or different, or the two R' groups, together with the nitrogen atom to which they are attached, form a 5-12 membered heterocyclic ring.

3. A compound according to claim 1, wherein $R_1$ is selected from the group consisting of OR', SR', SOR', $NH_2$, NHR', $N(R')2$, NHCOR', $N(COR')_2$ and $NHSO_2R'$, each R' group being independently selected from the group consisting of $C_1$-$C_6$ alkyl, $C_1$-$C_6$ haloalkyl, aryl (which may optionally be substituted with a group selected from $C_1$-$C_6$ alkyl, $C_1$-$C_6$ alkoxy and halogen), aralkyl (the aryl moiety of which may optionally be substituted with a group selected from $C_1$-$C_6$ alkyl, $C_1$-$C_6$ alkoxy and halogen), arylalkenyl (the aryl moiety of which may optionally be substituted with group selected from $C_1$-$C_6$ alkyl, $C_1$-$C_6$ alkoxy and halogen), and wherein when the group $R_1$ is a group of formula $N(R')_2$ or $N(COR')_2$, the two R' groups, together with the nitrogen atom to which they are attached, may form a 5-10 membered heterocyclic ring.

4. A compound according to claim 1, wherein $R_1$ is selected from the group consisting of $C_1$-$C_4$ alkoxy, $C_1$-$C_4$ alkylthio, $C_1$-$C_4$ alkylsulfinyl, amino, $C_1$-$C_4$ alkylamino di($C_1$-$C_4$ alkyl)amino, $C_1$-$C_4$ alkanoylamino, di($C_1$-$C_4$ alkanoyl)amino, $C_1$-$C_4$ haloalkanoylamino, arylamino (wherein the aryl moiety may optionally be substituted with a $C_1$-C4 alkoxy group), benzylamino (wherein the phenyl part of the benzyl moiety may optionally be substituted with a $C_1$-$C_4$ alkoxy group), cinnamoylamino or dicinnamoylamino (wherein the phenyl part of the or each cinnamoyl moiety may optionally be substituted with a $C_1$-$C_4$ alkoxy group), or a 5- to 7-membered nitrogen-containing heterocyclic ring attached to the remainder of the molecule via its nitrogen atom.

5. A compound according to claim 1, wherein $R_1$ is selected from methoxy, methylthio, methylsulfinyl, amino, methylamino, ethylamino, benzylamino, acetylamino, trifluoroacetylamino, diacetylamino, cinnamoylamino, dicinnamoylamino, p-methoxybenzylamino and piperidino.

6. A compound according to claim 1, wherein $R_1$ is selected from amino, beuzylamino, acetylamino, trifluoroacetylamino, diacetylamino, cinnamoylamino, dicinnamoylamino and p-methoxybenzylamino.

7. A compound according to claim 1, wherein $R_2$ is selected from the group consisting of OH, OR', SH, SR', SOR', SO2R', $NH_2$, NHR', $N(R')_2$, NHCOR', $N(COR')_2$, $NHSO_2R'$, C(=O)R', CO2H, CO2R', $C_1$-$C_{12}$ alkyl and $C_1$-$C_{12}$ haloalkyl, each R' group being independently selected from the group consisting of OH, $C_1$-$C_{12}$ alkyl, $C_1$-$C_{12}$ haloalkyl, aryl (which may optionally be substituted with a group selected from $C_1$-$C_6$ alkyl, $C_1$-$C_6$ alkoxy, $C_1$-$C_6$ alkylthio, $NH_2$, $C_1$-$C_6$ alkylamino, di(C1-$C_6$ alkyl)amino, $NO_2$, CN and halogen), aralkyl or arylalkenyl (the aryl moiety of which may optionally be substituted with a group selected from $C_1$-$C_6$ alkyl, $C_1$-$C_6$ alkoxy, $C_1$-$C_6$ alkylthio, $NH_2$, $C_1$-$C_6$ alkylamino, di($C_1$-$C_6$ alkyl)amino, $NO_2$, CN and halogen), and wherein when the group $R_2$ is a group of formula $N(R')_2$ or $N(COR')2$, each of the R' groups may be the same or different, or the two R' groups, together with the nitrogen atom to which they are attached, form a 5-12 membered heterocyclic ring.

8. A compound according to claim 1, wherein $R_2$ is selected from the group consisting of OR', SR', SOR', $NH_2$, NHR', $N(R')_2$, NHCOR', $N(COR')_2$ and $NHSO_2R'$, each R' group being independently selected from the group consisting of $C_1$-$C_6$ alkyl, $C_1$-$C_6$ haloalkyl, aryl (which may optionally be substituted with a group selected from $C_1$-$C_6$ alkyl, $C_1$-$C_6$ alkoxy and halogen), aralkyl (the aryl moiety of which may optionally be substituted with a group selected from $C_1$-$C_6$ alkyl, $C_1$-$C_6$ alkoxy and halogen), arylalkenyl (the aryl moiety of which may optionally be substituted with a group selected from $C_1$-$C_6$ alkyl, $C_1$-$C_6$ alkoxy and halogen), and wherein when the group $R_2$ is a group of formula $N(R')_2$ or $N(COR')_2$, the two R' groups, together with the nitrogen atom to which they are attached, may form a 5-10 membered heterocyclic ring.

9. A compound according to claim 1, wherein $R_2$ is selected from the group consisting of $C_1$-$C_4$ alkoxy, $C_1$-$C_4$ alkylthio, $C_1$-$C_4$ alkylsulfinyl, amino, $C_1$-$C_4$ alkylamino, di($C_1$-$C_4$ alkyl)amino, $C_1$-$C_4$ alkanoylamino, di($C_1$-$C_4$ alkanoyl)amino, $C_1$-$C_4$ haloalkanoylamino, arylamino (wherein the aryl moiety may optionally be substituted with a $C_1$-$C_4$ alkoxy group), benzylamino (wherein the phenyl part of the benzyl moiety may optionally be substituted with a $C_1$-$C_4$ alkoxy group), cinnamoylamino or dicinnamoylamino (wherein the phenyl part of the or each cinnamoyl moiety may optionally be substituted with a $C_1$-$C_4$ alkoxy group), or a 5- to 7-membered nitrogen-containing heterocyclic ring attached to the remainder of the molecule via its nitrogen atom.

10. A compound according to claim 1, wherein $R_2$ is selected from methylthio, methylsulfinyl, amino, methylamino, ethylamino, acetylamino, diacetylamino, cinnamoylamino, and p-methoxybenzylamino.

11. A compound according to claim 1, wherein $R_2$ is selected from amino, acetylamino, diacetylamino and p-methoxybenzylamino.

12. A compound according to claim 1, wherein $R_3$ is OH.

13. A compound according to claim 1, wherein $R_3$ is OMe.

14. A compound of the formula:

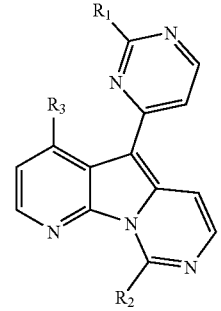

being a numbered compound in the following table where R', $R_2$ $R_3$ take the indicated meanings:

| compound number | $R^1$ | $R^2$ | $R^3$ |
| --- | --- | --- | --- |
| 13 | SMe | SMe | OMe |
| 14 | SOMe | SOMe | OMe |
| 15 | NHPMB | NHPMB | OMe |
| 16 | NHPMB | NHPMB | OH | where - NHPMB indicates p-methoxybenzylamino.

15. A process for producing a compound of formula (I):

(I)

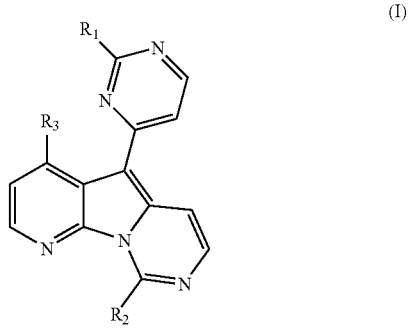

wherein:

R₁ and R₂ are each independently selected from the group consisting of H, OH, OR', SH, SR', SOR', SO₂R', NO₂, NH₂, NHR', N(R')₂, NHCOR', N(COR)₂, NHSO₂R', CN, halogen, C(=O)H, C(=O)R',CO₂H, CO₂R', $C_1$-$C_{12}$ alkyl, $C_1$-$C_{12}$ haloalkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic; and R₃ is selected from the group consisting of OH and OMe;

wherein each R' group is independently selected from the group consisting of OH, $C_1$-$C_{12}$ alkyl, $C_1$-$C_{12}$ haloalkyl, $C_2$-$C_{12}$ alkenyl, $C_2$-$C_{12}$ alkynyl, substituted or unsubstituted aryl, substituted or unsubstituted aralkyl, substituted or unsubstituted arylalkenyl and substituted or unsubstituted heteroaromatic, and wherein when the group R₁ or R₂ is a group of formula N(R')₂ or N(COR')₂, each of the R' groups may be the same or different, or the two R' groups, together with the nitrogen atom to which they are attached, may form a 5-14 membered heterocyclic ring;

the aryl group and the aryl moiety of the aralkyl and arylalkenyl group is a carbocyclic aryl group having from 6 to 14 carbon atoms in a carbocyclic ring or two or more fused rings;

the aralkyl group is a $C_1$-$C_6$ alkyl group which is substituted by an aryl group as defined above;

the arylalkenyl group is a $C_2$-$C_6$ alkenyl group which is substituted by an aryl group as defined above;

the heteroaromatic group is a heterocyclic aromatic group having from 5 to 14 ring atoms in one ring or two or more fused rings of which at least one ring atom is selected from the group consisting of nitrogen, oxygen and sulphur, and such a heterocyclic aromatic group fused with an aryl group as defined above;

the substituents on the aryl and heteroaromatic groups and the aryl moiety of the aralkyl and arylalkenyl groups are selected from the group consisting of $C_1$-$C_{12}$ alkyl, $C_1$-$C_{12}$ haloalkyl, $C_1$-$C_{12}$ alkoxy, $C_1$-$C_{12}$ alkylthio, NH₂, $C_1$-$C_6$ alkylamino, di($C_1$-$C_6$ alkyl)amino, $C_1$-$C_4$ alkanoylamino, di($C_1$-$C_4$ alkanoyl)amino, NO₂, CN and halogen; and wherein one or more of the tertiary amine nitrogen atoms of formula (I) is optionally quaternised, or a pharmaceutically acceptable salt thereof, the process comprising cyclising an intermediate of formula (II)

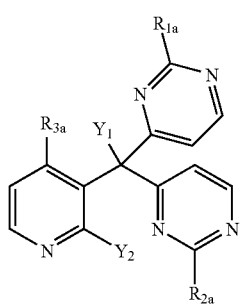

(II)

wherein: $R_{1a}$, $R_2$ and $R_{3a}$ represent any of the groups represented by $R_1$, $R_2$ and $R_3$ respectively, and all such groups where reactive functional groups are protected; and Y₁ and Y₂ are groups capable of being eliminated to produce a fused tricyclic pyridopyrrolopyrimidine ring structure, to give a compound of formula (III):

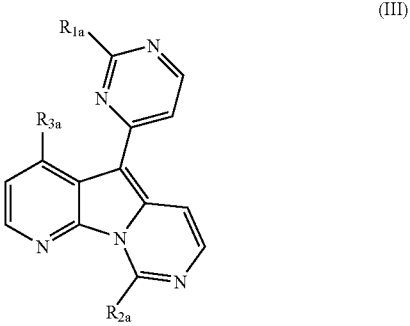

(III)

and, if necessary, converting any of the groups represented by $R_{1a}$, $R_{2a}$, and $R_{3a}$ to any of the groups represented by R₁, R₂ and R₃ respectively.

16. A process according to claim 15, wherein Y₁ is a hydroxy group.

17. A process according to claim 15, wherein Y₂ is a chlorine atom.

18. A process according to claim 15, wherein $R_{1a}$=$R_{2a}$.

19. A process according to claim 18, wherein $R_{1a}$ and $R_{2a}$ are methylthio groups.

20. A process according to claim 15, the process being acid-catalysed.

21. A process according to claim 15, the process comprising reaction of the intermediate of formula (II) with a trialkylsilane of formula $R_aR_bR_cSiH$ wherein $R_a$, $R_b$ and $R_c$ may be the same or different and each represents a $C_1$-$C_{12}$ alkyl group.

22. A process according to claim 15, wherein the intermediate of formula (II) is produced by reacting an intermediate compound of formula (IV):

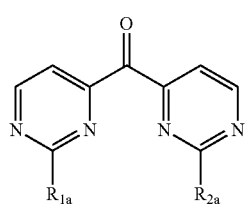

(IV)

wherein $R_{3a}$, and Y₂ are as defined in claim 14 and M is a metal, with a compound of formula (V):

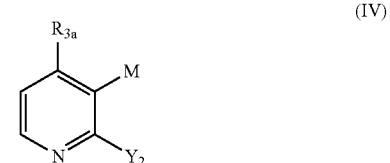

(V)

wherein $R_{1a}$ and $R_{2a}$ are as defined in claim 14.

23. A process according to claim 15, wherein the intermediate of formula (II) is produced by reacting an intermediate compound of formula (VI):

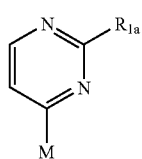

wherein R$_{1a}$ is as defined in claim 15 and M is a metal, with an intermediate compound of formula (VII)

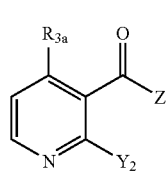

wherein R$_{3a}$ and Y$_2$ are as defined in claim 15, and Z is a leaving group.

24. A process for producing a compound of formula (I):

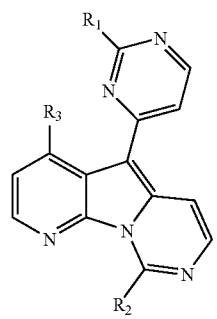

wherein:
R$_1$ and R$_2$ are each independently selected from the group consisting of H, OH, OR', SH, SR', SOR', SO$_2$R', NO$_2$, NH$_2$, NHR', N(R')$_2$, NHCOR', N(COR')$_2$, NHSO$_2$R', CN, halogen, C(=O)H, C(=O)R'CO$_2$H, CO$_2$R'C$_1$-C$_{12}$ alkyl, C$_1$-C$_{12}$ haloalkyl, C$_2$-C$_{12}$ alkenyl, C$_2$-C$_{12}$ alkynyl, substituted or unsubstituted aryl, substituted or unsubstituted aralkyl and substituted or unsubstituted heteroaromatic; and R$_3$ is selected from the group consisting of OH and OMe;
wherein each R' group is independently selected from the group consisting of OH, C$_1$-C$_{12}$ alkyl, C$_1$-C$_{12}$ haloalkyl, C$_2$-C$_{12}$ alkenyl, C$_2$-C$_{12}$ alkynyl, substituted or unsubstituted aryl, substituted or unsubstituted aralkyl, substituted or unsubstituted arylalkenyl and substituted or unsubstituted heteroaromatic,
and wherein when the group R$_1$ or R$_2$ is a group of formula N(R')$_2$ or N(COR')$_2$, each of the R' groups may be the same or different, or the two R' groups, together with the nitrogen atom to which they are attached, may form a 5-14 membered heterocyclic ring; the aryl group and the aryl moiety of the aralkyl and arylalkenyl group is a carbocyclic aryl group having from 6 to 14 carbon atoms in a carbocyclic ring or two or more fused rings;
the aralkyl group is a C$_1$-C$_6$ alkyl group which is substituted by an aryl group as defined above;
the arylalkenyl group is a C$_2$-C$_6$ alkenyl group which is substituted by an aryl group as defined above;
the heteroaromatic group is a heterocyclic aromatic group having from 5 to 14 ring atoms in one ring or two or more fused rings of which at least one ring atom is selected from the group consisting of nitrogen, oxygen and sulphur, and such a heterocyclic aromatic group fused with an aryl group as defined above;
the substituents on the aryl and heteroaromatic groups and the aryl moiety of the aralkyl and arylalkenyl groups are selected from the group consisting of C$_1$-C$_{12}$ alkyl, C$_1$-C$_{12}$ haloalkyl, C$_1$-C$_{12}$ alkoxy, C$_1$-C$_{12}$ alkylthio, NH$_2$, C$_1$-C$_6$ alkylamino, di(C$_1$-C$_6$ alkyl)amino, C$_1$-C$_4$ alkanoylamino, di(C$_1$-C$_4$ alkanoyl)amino, N$_2$, CN and halogen; and wherein one or more of the tertiary amine nitrogen atoms of formula (I) is optionally quaternised,
or a pharmaceutically acceptable salt thereof,
comprising the following steps:
a) conversion of a compound of formula (VIII):

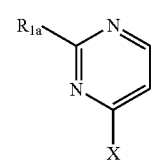

to a compound of formula (VI):

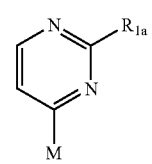

wherein R$_{1a}$ represents any of the groups represented by R$_1$, and all such groups where reactive functional groups are protected; X is a halogen atom, and M is a metal;
b) reaction of a compound of formula (VI) with a compound of formula L$_1$-CO-L$_2$, where L$_1$ and L$_2$ are the same or different and each represents a leaving group, to give a compound of formula (V):

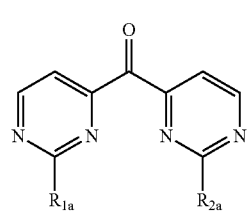

wherein R$_{1a}$ and R$_{2a}$ represent any of the groups represented by R$_1$ and R$_2$, respectively, and all such groups where reactive functional groups are protected;
c) reacting the compound of formula (V) with a compound of formula (IV):

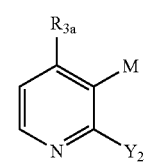

to form a compound of formula (II):

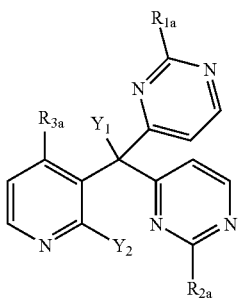

wherein:
- $R_{1a}$, $R_{2a}$ and $R_{3a}$ represent any of the groups represented by $R_1$, $R_2$ and $R_3$ respectively, and all such groups where reactive functional groups are protected; $Y_1$ and $Y_2$ are groups capable of being eliminated to produce a fused tricyclic pyridopyrrolopyrimidine ring structure; and M is a metal;
- d) cyclization of the compound of formula (II) to form a compound of formula (III):

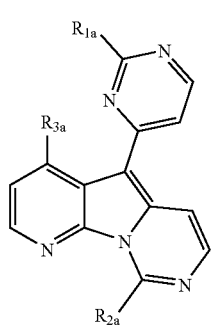

wherein:
- $R_{1a}$, $R_{2a}$ and $R_{3a}$ represent any of the groups represented by $R_1$, $R_2$ and $R_3$ respectively, and all such groups where reactive functional groups are protected;
- e) if necessary, converting any of the groups represented by $R_{1a}$, $R_{2a}$, and $R_{3a}$ to any of the groups represented by $R_1$, $R_2$ and $R_3$ respectively.

25. A process for producing a compound of formula (I):

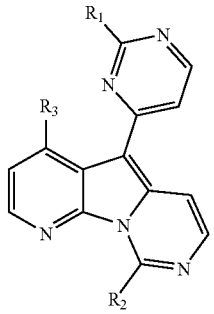

wherein:
$R_1$ and $R_2$ are each independently selected from the group consisting of H, OH, OR', SH, SR', SOR', $SO_2R'$, $NO_2$, $NH_2$, NHR', $N(R')_2$, NHCOR', $N(COR')_2$, $NHSO_2R'$, CN, halogen, C(=O)H, C(=O)R'$CO_2H$, $CO_2R'$, $C_1$-$C_{12}$ alkyl, $C_1$-$C_{12}$ haloalkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic; and $R_3$ is selected from the group consisting of OH and OMe;

wherein each R' group is independently selected from the group consisting of OH, $C_1$-$C_{12}$ alkyl, $C_1$-$C_{12}$, haloalkyl, $C_2$-$C_{12}$ alkenyl, $C_2$-$C_{12}$ alkynyl, substituted or unsubstituted aryl, substituted or unsubstituted aralkyl, substituted or unsubstituted arylalkenyl and substituted or unsubstituted heteroaromatic, and wherein when the group $R_1$ or $R_2$ is a group of formula $N(R')_2$ or $N(COR')_2$, each of the R' groups may be the same or different, or the two R' groups, together with the nitrogen atom to which they are attached, may form a 5-14 membered heterocyclic ring;

the aryl group and the aryl moiety of the aralkyl and arylalkenyl group is a carbocyclic aryl group having from 6 to 14 carbon atoms in a carbocyclic ring or two or more fused rings;

the aralkyl group is a $C_1$-$C_6$ alkyl group which is substituted by an aryl group as defined above;

the arylalkenyl group is a $C_2$-$C_6$ alkenyl group which is substituted by an aryl group as defined above;

the heteroaromatic group is a heterocyclic aromatic group having from 5 to 14 ring atoms in one ring or two or more fused rings of which at least one ring atom is selected from the group consisting of nitrogen, oxygen and sulphur, and such a heterocyclic aromatic group fused with an aryl group as defined above;

the substituents on the aryl and heteroaromatic groups and the aryl moiety of the aralkyl and arylalkenyl groups are selected from the group consisting of $C_1$-$C_{12}$ alkyl, $C_1$-$C_{12}$ haloalkyl, $C_1$-$C_{12}$ alkoxy, $C_1$-$C_{12}$ alkylthio, $NH_2$, $C_1$-$C_6$ alkylamino, di($C_1$-$C_6$ alkyl)amino, $C_1$-$C_4$ alkanoylamino, di($C_1$-$C_4$ alkanoyl)amino, $NO_2$, CN and halogen;

and wherein one or more of the tertiary amine nitrogen atoms of formula (I) is optionally quatemised, or a pharmaceutically acceptable salt thereof comprising the following steps:
a) converting a compound of formula (VIII):

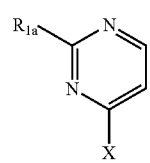

to a compound of formula (VI):

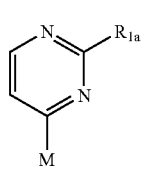

wherein $R_{1a}$ represents any of the groups represented by $R_1$, and all such groups where reactive functional groups are protected; X is a halogen atom, and M is a metal;

b) reacting the compound of formula (VI) with a compound of formula (VII):

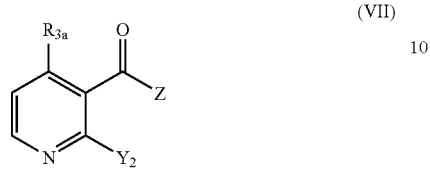

(VII)

to produce a compound of formula (II):

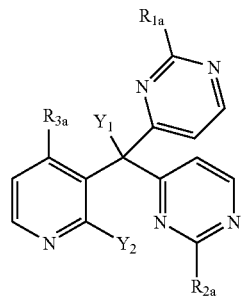

(II)

wherein:

$R_{1a}$, $R_{2a}$ and $R_{3a}$ represent any of the groups represented by $R_1$, $R_2$ and $R_3$ respectively, and all such groups where reactive functional groups are protected; $Y_1$ and $Y_2$ are groups capable of being eliminated to produce a fused tricyclic pyridopyrrolopyrimidine ring structure; M is a metal; and Z is a leaving group;

c) cyclization of the compound of formula (II) to form a compound of formula (III):

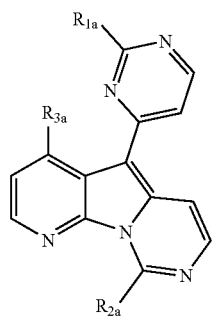

(III)

wherein:

$R_{1a}$, $R_{2a}$ and $R_{3a}$ represent any of the groups represented by $R_1$, $R_2$ and $R_3$ respectively, and all such groups where reactive functional groups are protected;

d) if necessary, converting any of the groups represented by $R_{1a}$, $R_{2a}$ and $R_{3a}$ to any of the groups represented by $R_1$, $R_2$ and $R_3$ respectively.

26. A process according to claim 15 for producing a compound of formula (I) wherein $R_1$ and $R_2$ are amino groups and $R_3$ is as defined in claim 15, said process comprising:

a) treating a compound of formula (III), wherein $R_{1a}$ and $R_{2a}$ are methylsulfinyl and $R_{3a}$ is as defined in claim 15, with a compound of formula $NH_2Prot$, where Prot is an amino-protecting group, to give a compound of formula (III), wherein $R_{1a}$ ai' id $R_{2a}$ are protected amino and $R_{3a}$ is as defined in claim 15, and b) removing the amino-protecting group to give a compound of formula (1) wherein $R_1$ and $R_2$ are amino groups and $R_3$ is as defined.

27. A process according to claim 15 for producing a compound of formula (I) wherein $R_1$ is a methylthio or amino group, $R_2$ is an amino group and $R_3$ is as defined in claim 15, said process comprising:

a) optionally, oxidising the compound of formula (III) wherein $R_{1a}$ and $R_{2a}$ are methylthio and $R_{3a}$ is as defined in claim 15 to a compound of formula (III) wherein $R_{1a}$ and $R_{2a}$ are methylsulfinyl; and b) treating the compound of formula (III) wherein $R_{1a}$ and $R_{2a}$ are methylthio or methylsulfinyl with a reagent selected from sodium azide and ammonia.

28. A process for producing a compound of formula (I):

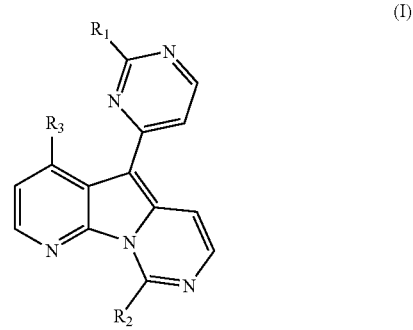

(I)

wherein:

$R_1$ and $R_2$ are each independently selected from the group consisting of $SCH_3$, $SOCH_3$, $SO_2CH3$, $NH_2$, and NH(4-methoxybenzyl); and $R_3$ is H;

the process comprising cyclising an intermediate of formula (II):

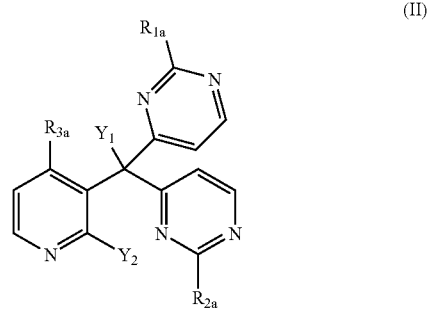

(II)

wherein:
each of $R_{1a}$ and $R_{2a}$ is $SCH_3$; $R_{3a}$ is hydrogen; $Y_1$ is H or OH; and $Y_2$ is chloro, to give a compound of formula (III):

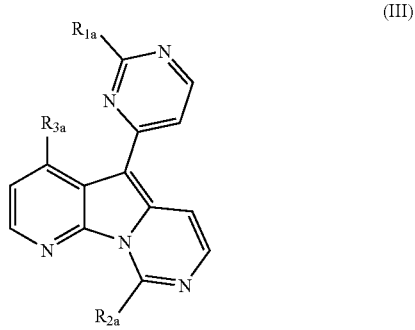

(III)

wherein each of $R_{1a}$ and $R_{2a}$ is SCH3; and $R_{3a}$ is hydrogen; and, if necessary, converting any of the groups represented by $R_{1a}$ and $R_{2a}$ to any of the groups represented by $R_1$ and $R_2$ in formula (I).

29. A process according to claim 28, wherein $Y_1$ is a hydroxy group.

30. A process according to claim 28, the process being acid-catalysed.

31. A process according to claim 28, the process comprising reaction of the intermediate of formula (II) with triethylsilane.

32. A process according to claim 28, wherein the intermediate of formula (II) is produced by reacting an intermediate compound of formula (VI):

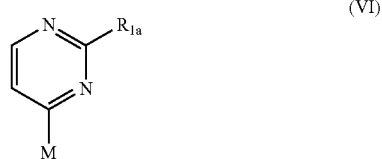

(VI)

wherein $R_{1a}$ is $SCH_3$ and M is lithium, with an intermediate compound of formula (VII)

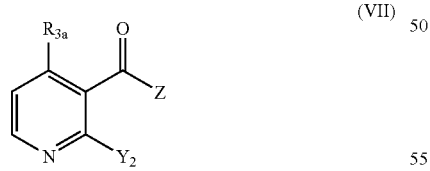

(VII)

wherein $R_{3a}$ is H, and $Y_2$ and Z are both chloro.

33. A process according to claim 28 for producing a compound of formula (I) wherein each of $R_1$ and $R_2$ is a 4-methoxybenzylamino group, said process comprising:
a) oxidising the compound of formula (III) to provide a compound of formula (I) wherein $R_1$ and $R_2$ are each independently $SOCH_3$ or $SO_2CH_3$; and
b) treating the compound of formula (I) wherein $R_1$ and $R_2$ are each independently $SOCH_3$ or $SO_2CH_3$ with 4-methoxyberizylamine; thereby providing a compound of formula (I) wherein each of $R_1$ and $R_2$ is a 4-methoxybenzylamino group.

34. The process of claim 33, further comprising removing the 4-methoxybenzyl group to give a compound of formula (I) wherein each of $R_1$ and $R_2$ is an amino group.

35. The process of claim 33, wherein step a) provides a compound of formula (I), wherein each of $R_1$ and $R_2$ is $SOCH_3$.

36. A process for producing a compound of formula (I):

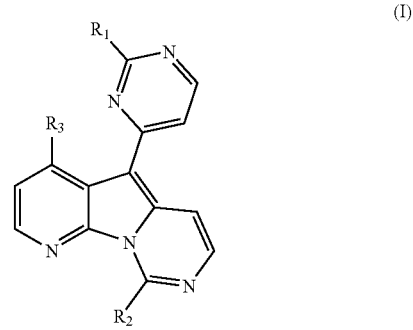

(I)

wherein:
$R_1$ and $R_2$ are each independently selected from the group consisting of $SCH_3$, $SOCH_3$, $S_2CH_3$, $NH_2$, and NH(4-methoxybenzyl); and
$R_3$ is H;
comprising the following steps:
a) converting a compound of formula (VIII):

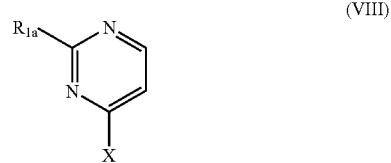

(VIII)

to a compound of formula (VI):

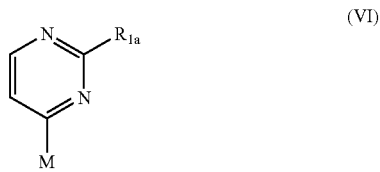

(VI)

wherein $R_{1a}$ is $SCH_3$; X is chloro or iodo; and M is lithium;
b) reacting the compound of formula (VI) with a compound of formula (VII):

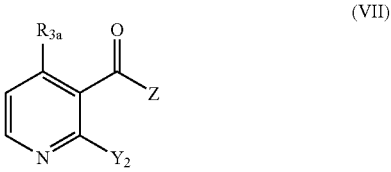

(VII)

to produce a compound of formula (II):

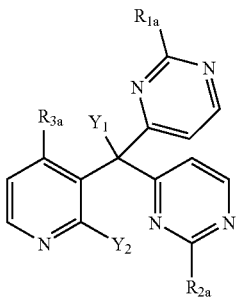

wherein:
each of $R_{1a}$ and $R_{2a}$ is $SCH_3$; $R_{3a}$ is hydrogen; $Y_1$ is H or OH; and $Y_2$ and Z are both chloro;
c) cyclization of the compound of formula (II) to form a compound of formula (III):

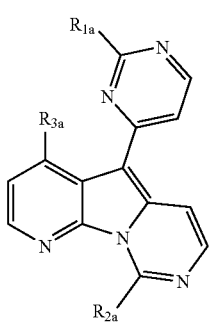

wherein:
each of $R_{1a}$ and $R_{2a}$ is $SCH_3$; and $R_{3a}$ is hydrogen;
d) if necessary, converting any of the groups represented by $R_{1a}$ and $R_{2a}$ to any of the groups represented by $R_1$ and $R_2$ in formula (I).

37. A compound of formula (II):

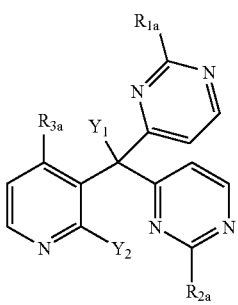

wherein
$R_{1a}$ and $R_{2a}$ are each independently selected from the group consisting of H, OH, OR', SH, SR', SOR', $SO_2R'$, $NO_2$, $NH_2$, NHR', $N(R')_2$, NHCOR', $N(COR')_2$, $NHSO_2R'$, CN, halogen, C(=O)H, C(=O)R', $C_2H$, $CO_2R'$, $C_1$-$C_{12}$ alkyl, $C_1$-$C_{12}$ haloalkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic; and $R_{3a}$ is selected from the group consisting of OH and OMe;
wherein each R' group is independently selected from the group consisting of OH, $C_1$-$C_{12}$ alkyl, $C_1$-$C_{12}$ haloalkyl, $C_2$-$C_{12}$ alkenyl, $C_2$-$C_{12}$ alkynyl, substituted or unsubstituted aryl, substituted or unsubstituted aralkyl, substituted or unsubstituted arylalkenyl and substituted or unsubstituted heteroaromatic, and wherein when the group $R_{1a}$ or $R_{2a}$ is a group of formula $N(R')_2$ or $N(COR')_2$, each of the R' groups may be the same or different, or the two R' groups, together with the nitrogen atom to which they are attached, may form a 5-14 membered heterocyclic ring;

the aryl group and the aryl moiety of the aralkyl and arylalkenyl group is a carbocyclic aryl group having from 6 to 14 carbon atoms in a carbocyclic ring or two or more fused rings;

the aralkyl group is a $C_1$-$C_6$ alkyl group which is substituted by an aryl group as defined above;

the arylalkenyl group is a $C_2$-$C_6$ alkenyl group which is substituted by an aryl group as defined above;

the heteroaromatic group is a heterocyclic aromatic group having from 5 to 14 ring atoms in one ring or two or more fused rings of which at least one ring atom is selected from the group consisting of nitrogen, oxygen and sulphur, and such a heterocyclic aromatic group fused with an aryl group as defined above;

the substituents on the aryl and heteroaromatic groups and the aryl moiety of the aralkyl and arylalkenyl groups are selected from the group consisting of $C_1$-$C_{12}$ alkyl, $C_1$-$C_{12}$ haloalkyl, $C_1$-$C_{12}$ alkoxy, $C_1$-$C_{12}$ alkylthio, NH2, $C_1$-$C_6$ alkylamino, di($C_1$-$C_6$ alkyl)amino, $C_1$-$C_4$ alkanoylamino, di($C_1$-$C_4$ alkanoyl)amino, $NO_2$, CN and halogen;

and wherein one or more of the tertiary amine nitrogen atoms of formula (II) is optionally quaternised;

hydroxy, acetate, methanesulfonate, p-toluenesulfonate, or trifluoromethanesulfonate; and $Y_2$ is halogen.

38. A compound according to claim 37, wherein $Y_1$ is a hydroxy group.

39. A compound according to claim 37, wherein $Y_2$ is a chlorine atom.

40. A compound according to claim 37, wherein $R_{1a}$ $R_{2a}$.

41. A compound according to claim 40, wherein $R_{1a}$ and $R_{2a}$ are methylthio groups.

42. A pharmaceutical composition comprising an effective amount of a pharmacologically active compound together with a carrier or diluent therefor, wherein said pharmacologically active compound is a compound according to claim 1.

43. A method for the treatment of a cancer selected from lung cancer, colon cancer, ovarian cancer, kidney cancer, prostate cancer, breast cancer and melanoma in a mammal, which comprises administering to a mammal in need of such treatment an effective amount of a compound of formula (I), as defined in claim 1.

44. A method for the treatment of a cancer selected from ovarian cancer, kidney cancer, prostate cancer, breast cancer and melanoma in a mammal, which comprises administering to a mammal in need of such treatment an effective amount of a compound of formula (I):

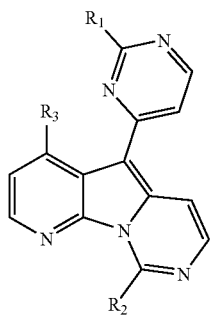

(I)

wherein:
R$_1$ and R$_2$ are each independently selected from the group consisting of H, OH, OR', SH, SR', SOR', S$_2$R', NO$_2$, NH$_2$, NHR', N(R')$_2$, NHCOR', N(COR')$_2$, NHSO$_2$R', CN, halogen, C(=O)H, C(=O)R', CO$_2$H, CO$_2$R'C$_1$-C$_{12}$ alkyl, C$_1$-C$_{12}$ haloalkyl, C$_2$-C$_{12}$ alkenyl, C$_2$-C$_{12}$ alkynyl, substituted or unsubstituted aryl, substituted or unsubstituted aralkyl and substituted or unsubstituted heteroaromatic; and R$_3$ is selected from the group consisting of OH and OMe;

wherein each R' group is independently selected from the group consisting of OH, C$_1$-C$_{12}$ alkyl, C$_1$-C$_{12}$ haloalkyl, C$_2$-C$_{12}$ alkenyl, C$_2$-C$_{12}$ alkynyl, substituted or unsubstituted aryl, substituted or unsubstituted aralkyl, substituted or unsubstituted arylalkenyl and substituted or unsubstituted heteroaromatic, and wherein when the group R$_1$ or R$_2$ is a group of formula N(R')$_2$ or N(COR')$_2$, each of the R' groups may be the same or different, or the two R' groups, together with the nitrogen atom to which they are attached, may form a 5-14 membered heterocyclic ring;

the aryl group and the aryl moiety of the aralkyl and arylalkenyl group is a carbocyclic aryl group having from 6 to 14 carbon atoms in a carbocyclic ring or two or more fused rings;

the aralkyl group is a C$_1$-C$_6$ alkyl group which is substituted by an aryl group as defined above;

the arylalkenyl group is a C$_2$-C$_6$ alkenyl group which is substituted by an aryl group as defined above;

the heteroaromatic group is a heterocyclic aromatic group having from 5 to 14 ring atoms in one ring or two or more fused rings of which at least one ring atom is selected from the group consisting of nitrogen, oxygen and sulphur, and such a heterocyclic aromatic group fused with an aryl group as defined above;

the substituents on the aryl and heteroaromatic groups and the aryl moiety of the aralkyl and arylalkenyl groups are selected from the group consisting of C$_1$-C$_{12}$ alkyl, C$_1$-C$_{12}$ haloalkyl, C$_1$-C$_{12}$ alkoxy, C$_1$-C$_{12}$ alkylthio, NH$_2$, C$_1$-C$_6$ alkylamino, di(C$_1$-C$_6$ alkyl)amino, C$_1$-C$_4$ alkanoylamino, di(C$_1$-C$_4$ alkanoyl)amino, NO$_2$, CN and halogen;

and wherein one or more of the tertiary amine nitrogen atoms of formula (I) is optionally quaternised; or a pharmaceutically acceptable salt thereof.

45. A method for the treatment of a cancer selected from lung cancer, colon cancer, ovarian cancer, kidney cancer, prostate cancer, breast cancer and melanoma in a mammal, which comprises administering to a mammal in need of such treatment an effective amount of a compound as defined in claim 14.

* * * * *